US012023523B2

(12) United States Patent
Olcott et al.

(10) Patent No.: US 12,023,523 B2
(45) Date of Patent: *Jul. 2, 2024

(54) SYSTEMS AND METHODS FOR FAULT DETECTION IN EMISSION-GUIDED RADIOTHERAPY

(71) Applicant: RefleXion Medical, Inc., Hayward, CA (US)

(72) Inventors: Peter Demetri Olcott, Los Gatos, CA (US); Matthew Francis Bieniosek, Danville, CA (US)

(73) Assignee: RefleXion Medical, Inc., Hayward, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/056,188

(22) Filed: Nov. 16, 2022

(65) Prior Publication Data
US 2023/0256268 A1  Aug. 17, 2023

Related U.S. Application Data

(63) Continuation of application No. 17/238,113, filed on Apr. 22, 2021, now Pat. No. 11,511,133, which is a
(Continued)

(51) Int. Cl.
*A61N 5/10* (2006.01)

(52) U.S. Cl.
CPC ......... *A61N 5/1075* (2013.01); *A61N 5/1049* (2013.01); *A61N 5/1064* (2013.01);
(Continued)

(58) Field of Classification Search
CPC .. A61N 5/1075; A61N 5/1049; A61N 5/1064; A61N 5/1081; A61N 2005/1052; A61N 2005/1095
See application file for complete search history.

(56) References Cited

U.S. PATENT DOCUMENTS 3,418,475 A   12/1968  Hudgens
3,668,399 A   6/1972   Cahill et al.
(Continued)

FOREIGN PATENT DOCUMENTS

CN   1681436 A   10/2005
CN   1799509 A   7/2006
(Continued)

OTHER PUBLICATIONS

Black, Q.C. et al. (2004). "Defining a Radiotherapy Target with positron emission tomography," Int. J. Radiation Oncology Biol. Phys. 60:1272-1282.
(Continued)

*Primary Examiner* — Kiho Kim
(74) *Attorney, Agent, or Firm* — COOLEY LLP

(57) ABSTRACT

Disclosed herein are systems and methods for monitoring calibration of positron emission tomography (PET) systems. In some variations, the systems include an imaging assembly having a gantry comprising a plurality of positron emission detectors. A housing may be coupled to the gantry, and the housing may include a bore and a radiation source holder spaced away from a patient scan region within the bore. A processor may be configured to receive positron emission data from the positron emission detectors and to distinguish the positron emission data from the radiation source holder and from the patient scan region. A fault signal may be generated when the positron emission data from the radiation source holder exceeds one or more threshold parameters or criteria.

19 Claims, 12 Drawing Sheets

Related U.S. Application Data continuation of application No. 16/818,325, filed on Mar. 13, 2020, now Pat. No. 11,007,384, which is a continuation of application No. 16/100,054, filed on Aug. 9, 2018, now Pat. No. 10,603,515.

(60) Provisional application No. 62/543,140, filed on Aug. 9, 2017.

(52) U.S. Cl.
CPC .... *A61N 5/1081* (2013.01); *A61N 2005/1052* (2013.01); *A61N 2005/1095* (2013.01)

(56) References Cited

U.S. PATENT DOCUMENTS

| | | |
|---|---|---|
| 3,767,883 A | 10/1973 | Staats |
| 3,794,840 A | 2/1974 | Scott |
| 3,869,615 A | 3/1975 | Hoover et al. |
| 3,906,233 A | 9/1975 | Vogel |
| 4,241,644 A | 12/1980 | Schertler |
| 4,246,488 A | 1/1981 | Hura |
| 4,361,902 A | 11/1982 | Brandt et al. |
| 4,389,569 A | 6/1983 | Hattori et al. |
| 4,503,331 A | 3/1985 | Kovacs, Jr. et al. |
| 4,529,882 A | 7/1985 | Lee |
| 4,563,582 A | 1/1986 | Mullani |
| 4,575,868 A | 3/1986 | Ueda et al. |
| 4,628,499 A | 12/1986 | Hammett |
| 4,642,464 A | 2/1987 | Mullani |
| 4,647,779 A | 3/1987 | Wong |
| 4,677,299 A | 6/1987 | Wong |
| 4,771,785 A | 9/1988 | Duer |
| 4,794,629 A | 12/1988 | Pastyr et al. |
| 4,868,844 A | 9/1989 | Nunan |
| 5,075,554 A | 12/1991 | Yunker et al. |
| 5,099,505 A | 3/1992 | Seppi et al. |
| 5,117,445 A | 5/1992 | Seppi et al. |
| 5,168,532 A | 12/1992 | Seppi et al. |
| 5,206,512 A | 4/1993 | Iwao |
| 5,207,223 A | 5/1993 | Adler |
| 5,272,344 A | 12/1993 | Williams |
| 5,317,616 A | 5/1994 | Swerdloff et al. |
| 5,329,567 A | 7/1994 | Ikebe |
| 5,351,280 A | 9/1994 | Swerdloff et al. |
| 5,390,225 A | 2/1995 | Hawman |
| 5,394,452 A | 2/1995 | Swerdloff et al. |
| 5,396,534 A | 3/1995 | Thomas |
| 5,418,827 A | 5/1995 | Deasy et al. |
| 5,442,675 A | 8/1995 | Swerdloff et al. |
| 5,548,627 A | 8/1996 | Swerdloff et al. |
| 5,577,026 A | 11/1996 | Gordon et al. |
| 5,596,619 A | 1/1997 | Carol |
| 5,661,773 A | 8/1997 | Swerdloff et al. |
| 5,668,371 A | 9/1997 | Deasy et al. |
| 5,724,400 A | 3/1998 | Swerdloff et al. |
| 5,748,703 A | 5/1998 | Cosman |
| 5,751,781 A | 5/1998 | Brown et al. |
| 5,757,881 A | 5/1998 | Hughes |
| 5,813,985 A | 9/1998 | Carroll |
| 5,818,902 A | 10/1998 | Yu |
| 5,851,182 A | 12/1998 | Sahadevan |
| 5,889,834 A | 3/1999 | Vilsmeier et al. |
| 5,917,883 A | 6/1999 | Khutoryansky et al. |
| 5,937,028 A | 8/1999 | Tybinkowski et al. |
| 5,946,425 A | 8/1999 | Bove, Jr. et al. |
| 6,137,114 A | 10/2000 | Rohe et al. |
| 6,180,943 B1 | 1/2001 | Lange |
| 6,184,530 B1 | 2/2001 | Hines et al. |
| 6,188,748 B1 | 2/2001 | Pastyr et al. |
| 6,255,655 B1 | 7/2001 | McCroskey et al. |
| 6,260,005 B1 | 7/2001 | Yang et al. |
| 6,271,517 B1 | 8/2001 | Kroening, Jr. et al. |
| 6,281,505 B1 | 8/2001 | Hines et al. |
| 6,385,288 B1 | 5/2002 | Kanematsu |
| 6,396,902 B2 | 5/2002 | Tybinkowski et al. |
| 6,438,202 B1 | 8/2002 | Olivera et al. |
| 6,449,331 B1 | 9/2002 | Nutt et al. |
| 6,449,340 B1 | 9/2002 | Tybinkowski et al. |
| 6,455,856 B1 | 9/2002 | Gagnon |
| 6,459,769 B1 | 10/2002 | Cosman |
| 6,504,899 B2 | 1/2003 | Pugachev et al. |
| 6,560,311 B1 | 5/2003 | Shepard et al. |
| 6,618,467 B1 | 9/2003 | Ruchala et al. |
| 6,624,451 B2 | 9/2003 | Ashley et al. |
| 6,628,744 B1 | 9/2003 | Luhta et al. |
| 6,661,866 B1 | 12/2003 | Limkeman et al. |
| 6,696,694 B2 | 2/2004 | Pastyr et al. |
| 6,700,949 B2 | 3/2004 | Susami et al. |
| 6,714,076 B1 | 3/2004 | Kalb |
| 6,730,924 B1 | 5/2004 | Pastyr et al. |
| 6,735,277 B2 | 5/2004 | McNutt et al. |
| 6,778,636 B1 | 8/2004 | Andrews |
| 6,792,078 B2 | 9/2004 | Kato et al. |
| 6,794,653 B2 | 9/2004 | Wainer et al. |
| 6,810,103 B1 | 10/2004 | Tybinkowski et al. |
| 6,810,108 B2 | 10/2004 | Clark et al. |
| 6,831,961 B1 | 12/2004 | Tybinkowski et al. |
| 6,865,254 B2 | 3/2005 | Nafstadius |
| 6,888,919 B2 | 5/2005 | Graf |
| 6,914,959 B2 | 7/2005 | Bailey et al. |
| 6,934,363 B2 | 8/2005 | Seufert |
| 6,965,661 B2 | 11/2005 | Kojima et al. |
| 6,976,784 B2 | 12/2005 | Kojima et al. |
| 6,990,175 B2 | 1/2006 | Nakashima et al. |
| 7,020,233 B1 | 3/2006 | Tybinkowski et al. |
| 7,026,622 B2 | 4/2006 | Kojima et al. |
| 7,085,347 B2 | 8/2006 | Mihara et al. |
| 7,110,808 B2 | 9/2006 | Adair |
| 7,129,495 B2 | 10/2006 | Williams et al. |
| 7,154,096 B2 | 12/2006 | Amano |
| 7,167,542 B2 | 1/2007 | Juschka et al. |
| 7,177,386 B2 | 2/2007 | Mostafavi et al. |
| 7,188,999 B2 | 3/2007 | Mihara et al. |
| 7,191,100 B2 | 3/2007 | Mostafavi |
| 7,199,382 B2 | 4/2007 | Rigney et al. |
| 7,227,925 B1 | 6/2007 | Mansfield et al. |
| 7,242,750 B2 | 7/2007 | Tsujita |
| 7,263,165 B2 | 8/2007 | Ghelmansarai |
| 7,265,356 B2 | 9/2007 | Pelizzari et al. |
| 7,280,633 B2 | 10/2007 | Cheng et al. |
| 7,291,840 B2 | 11/2007 | Fritzler et al. |
| 7,297,958 B2 | 11/2007 | Kojima et al. |
| 7,298,821 B2 | 11/2007 | Ein-Gal |
| 7,301,144 B2 | 11/2007 | Williams et al. |
| 7,310,410 B2 | 12/2007 | Sohal et al. |
| 7,331,713 B2 | 2/2008 | Moyers |
| 7,338,207 B2 | 3/2008 | Gregerson et al. |
| 7,356,112 B2 | 4/2008 | Brown et al. |
| 7,367,955 B2 | 5/2008 | Zhang et al. |
| 7,386,099 B1 | 6/2008 | Kasper et al. |
| 7,397,901 B1 | 7/2008 | Johnsen |
| 7,397,902 B2 | 7/2008 | Seeber et al. |
| 7,405,404 B1 | 7/2008 | Shah |
| 7,412,029 B2 | 8/2008 | Myles |
| 7,433,503 B2 | 10/2008 | Cherek et al. |
| 7,439,509 B1 | 10/2008 | Grazioso et al. |
| 7,446,328 B2 | 11/2008 | Rigney et al. |
| 7,453,983 B2 | 11/2008 | Schildkraut et al. |
| 7,453,984 B2 | 11/2008 | Chen et al. |
| 7,469,035 B2 | 12/2008 | Keall et al. |
| 7,496,181 B2 | 2/2009 | Mazin et al. |
| 7,519,162 B2 | 4/2009 | Hoffmann |
| 7,545,911 B2 | 6/2009 | Rietzel et al. |
| 7,555,103 B2 | 6/2009 | Johnsen |
| 7,558,378 B2 | 7/2009 | Juschka et al. |
| 7,560,698 B2 | 7/2009 | Rietzel |
| 7,564,951 B2 | 7/2009 | Hasegawa et al. |
| 7,596,209 B2 | 9/2009 | Perkins |
| 7,620,444 B2 | 11/2009 | Le et al. |
| 7,627,082 B2 | 12/2009 | Kojima et al. |
| 7,639,853 B2 | 12/2009 | Olivera et al. |
| 7,649,981 B2 | 1/2010 | Seppi et al. |
| 7,656,999 B2 | 2/2010 | Hui et al. |

(56) References Cited

U.S. PATENT DOCUMENTS

| | | |
|---|---|---|
| 7,679,049 B2 | 3/2010 | Rietzel |
| 7,711,087 B2 | 5/2010 | Mostafavi |
| 7,715,606 B2 | 5/2010 | Jeung et al. |
| 7,742,575 B2 | 6/2010 | Bourne |
| 7,755,054 B1 | 7/2010 | Shah et al. |
| 7,755,055 B2 | 7/2010 | Schilling |
| 7,755,057 B2 | 7/2010 | Kim |
| 7,769,430 B2 | 8/2010 | Mostafavi |
| 7,778,691 B2 | 8/2010 | Zhang et al. |
| 7,783,007 B2 | 8/2010 | Echner |
| 7,783,335 B2 | 8/2010 | Le Corre |
| 7,792,252 B2 | 9/2010 | Bohn |
| 7,795,590 B2 | 9/2010 | Takahashi et al. |
| 7,800,070 B2 | 9/2010 | Weinberg et al. |
| 7,820,975 B2 | 10/2010 | Laurence et al. |
| 7,820,989 B2 | 10/2010 | Sommer |
| 7,831,073 B2 | 11/2010 | Fu et al. |
| 7,839,972 B2 | 11/2010 | Ruchala et al. |
| 7,847,274 B2 | 12/2010 | Kornblau et al. |
| 7,869,562 B2 | 1/2011 | Khamene et al. |
| 7,869,862 B2 | 1/2011 | Seppi et al. |
| 7,885,371 B2 | 2/2011 | Thibault et al. |
| 7,939,808 B1 | 5/2011 | Shah et al. |
| 7,942,843 B2 | 5/2011 | Tune et al. |
| 7,952,079 B2 | 5/2011 | Neustadter et al. |
| 7,957,507 B2 | 6/2011 | Cadman |
| 7,965,819 B2 | 6/2011 | Nagata |
| 7,983,380 B2 | 7/2011 | Guertin et al. |
| 8,017,915 B2 | 9/2011 | Mazin |
| 8,019,042 B2 | 9/2011 | Shukla et al. |
| 8,059,782 B2 | 11/2011 | Brown |
| 8,060,177 B2 | 11/2011 | Hamill |
| 8,063,376 B2 | 11/2011 | Maniawski et al. |
| 8,090,074 B2 | 1/2012 | Filiberti et al. |
| 8,093,568 B2 | 1/2012 | Mackie et al. |
| 8,116,427 B2 | 2/2012 | Kojima et al. |
| 8,139,713 B2 | 3/2012 | Janbakhsh |
| 8,139,714 B1 | 3/2012 | Sahadevan |
| 8,144,962 B2 | 3/2012 | Busch et al. |
| 8,148,695 B2 | 4/2012 | Takahashi et al. |
| 8,148,703 B2 | 4/2012 | Sommer |
| 8,160,205 B2 | 4/2012 | Saracen et al. |
| 8,193,508 B2 | 6/2012 | Shchory et al. |
| 8,198,600 B2 | 6/2012 | Neustadter et al. |
| 8,232,535 B2 | 7/2012 | Olivera et al. |
| 8,239,002 B2 | 8/2012 | Neustadter et al. |
| 8,269,195 B2 | 9/2012 | Rigney et al. |
| 8,278,633 B2 | 10/2012 | Nord et al. |
| 8,280,002 B2 | 10/2012 | Bani-Hashemi et al. |
| 8,295,435 B2 | 10/2012 | Wang et al. |
| 8,295,906 B2 | 10/2012 | Saunders et al. |
| 8,303,505 B2 | 11/2012 | Webler et al. |
| 8,304,738 B2 | 11/2012 | Gagnon et al. |
| 8,306,185 B2 | 11/2012 | Bal et al. |
| 8,311,185 B2 | 11/2012 | Seppi et al. |
| 8,335,296 B2 | 12/2012 | Dehler et al. |
| 8,357,903 B2 | 1/2013 | Wang et al. |
| 8,384,049 B1 | 2/2013 | Broad |
| 8,395,127 B1 | 3/2013 | Frach et al. |
| 8,406,844 B2 | 3/2013 | Ruchala et al. |
| 8,406,851 B2 | 3/2013 | West et al. |
| 8,442,287 B2 | 5/2013 | Fordyce, II et al. |
| 8,447,387 B2 | 5/2013 | Xu et al. |
| 8,461,538 B2 | 6/2013 | Mazin |
| 8,461,539 B2 | 6/2013 | Yamaya et al. |
| 8,467,497 B2 | 6/2013 | Lu et al. |
| 8,483,803 B2 | 7/2013 | Partain et al. |
| 8,509,383 B2 | 8/2013 | Lu et al. |
| 8,520,800 B2 | 8/2013 | Wilfley et al. |
| 8,536,547 B2 | 9/2013 | Maurer, Jr. et al. |
| 8,537,373 B2 | 9/2013 | Humphrey |
| 8,571,639 B2 | 10/2013 | Mostafavi |
| 8,581,196 B2 | 11/2013 | Yamaya et al. |
| 8,588,367 B2 | 11/2013 | Busch et al. |
| 8,594,769 B2 | 11/2013 | Mostafavi |
| 8,606,349 B2 | 12/2013 | Rousso et al. |
| 8,617,422 B2 | 12/2013 | Koschan et al. |
| 8,641,592 B2 | 2/2014 | Yu |
| 8,664,610 B2 | 3/2014 | Chuang |
| 8,664,618 B2 | 3/2014 | Yao |
| 8,712,012 B2 | 4/2014 | O'Connor |
| 8,745,789 B2 | 6/2014 | Saracen et al. |
| 8,748,825 B2 | 6/2014 | Mazin |
| 8,767,917 B2 | 7/2014 | Ruchala et al. |
| 8,788,020 B2 | 7/2014 | Mostafavi et al. |
| 8,816,307 B2 | 8/2014 | Kuusela et al. |
| 8,873,710 B2 | 10/2014 | Ling et al. |
| 8,884,240 B1 | 11/2014 | Shah et al. |
| 8,992,404 B2 | 3/2015 | Graf et al. |
| 9,061,141 B2 | 6/2015 | Brunker et al. |
| 9,155,909 B2 | 10/2015 | Ishikawa |
| 9,179,982 B2 | 11/2015 | Kunz et al. |
| 9,205,281 B2 | 12/2015 | Mazin |
| 9,232,928 B2 | 1/2016 | Mostafavi |
| 9,248,312 B2 | 2/2016 | Li et al. |
| 9,360,570 B2 | 6/2016 | Rothfuss et al. |
| 9,370,672 B2 | 6/2016 | Parsai et al. |
| 9,437,339 B2 | 9/2016 | Echner |
| 9,437,340 B2 | 9/2016 | Echner et al. |
| 9,498,167 B2 | 11/2016 | Mostafavi et al. |
| 9,560,970 B2 | 2/2017 | Rose et al. |
| 9,575,192 B1 | 2/2017 | Ng et al. |
| 9,649,509 B2 | 5/2017 | Mazin et al. |
| 9,694,208 B2 | 7/2017 | Mazin et al. |
| 9,697,980 B2 | 7/2017 | Ogura et al. |
| 9,731,148 B2 | 8/2017 | Olivera et al. |
| 9,820,700 B2 | 11/2017 | Mazin |
| 9,878,180 B2 | 1/2018 | Schulte et al. |
| 9,886,534 B2 | 2/2018 | Wan et al. |
| 9,952,878 B2 | 4/2018 | Grimme et al. |
| 9,974,494 B2 | 5/2018 | Mostafavi et al. |
| 10,159,853 B2 | 12/2018 | Kuusela et al. |
| 10,327,716 B2 | 6/2019 | Mazin |
| 10,478,133 B2 | 11/2019 | Levy et al. |
| 10,603,515 B2 | 3/2020 | Olcott et al. |
| 10,646,188 B2 | 5/2020 | Mostafavi et al. |
| 10,695,586 B2 | 6/2020 | Harper et al. |
| 10,745,253 B2 | 8/2020 | Saracen et al. |
| 10,795,037 B2 | 10/2020 | Olcott et al. |
| 10,959,686 B2 | 3/2021 | Mazin |
| 11,007,384 B2 | 5/2021 | Olcott et al. |
| 11,287,540 B2 | 3/2022 | Olcott et al. |
| 11,309,072 B2 | 4/2022 | Carmi |
| 11,511,133 B2 | 11/2022 | Olcott et al. |
| 11,520,415 B2 | 12/2022 | Douglas et al. |
| 11,627,920 B2 | 4/2023 | Mazin |
| 11,642,027 B2 | 5/2023 | Otto |
| 11,675,097 B2 | 6/2023 | Olcott et al. |
| 2002/0051513 A1 | 5/2002 | Pugachev et al. |
| 2002/0148970 A1 | 10/2002 | Wong et al. |
| 2002/0163994 A1 | 11/2002 | Jones |
| 2002/0191734 A1 | 12/2002 | Kojima et al. |
| 2002/0193685 A1 | 12/2002 | Mate et al. |
| 2003/0036700 A1 | 2/2003 | Weinberg |
| 2003/0043951 A1 | 3/2003 | Akers |
| 2003/0058984 A1 | 3/2003 | Susami et al. |
| 2003/0080298 A1 | 5/2003 | Karplus et al. |
| 2003/0105397 A1 | 6/2003 | Tumer et al. |
| 2003/0128801 A1 | 7/2003 | Eisenberg et al. |
| 2003/0219098 A1 | 11/2003 | McNutt et al. |
| 2004/0024300 A1 | 2/2004 | Graf |
| 2004/0030246 A1 | 2/2004 | Townsend et al. |
| 2004/0037390 A1 | 2/2004 | Mihara et al. |
| 2004/0057557 A1 | 3/2004 | Nafstadius |
| 2004/0116804 A1 | 6/2004 | Mostafavi |
| 2004/0158416 A1 | 8/2004 | Slates |
| 2004/0162457 A1 | 8/2004 | Maggiore et al. |
| 2004/0218719 A1 | 11/2004 | Brown et al. |
| 2005/0028279 A1 | 2/2005 | de Mooy |
| 2005/0104001 A1 | 5/2005 | Shah |
| 2005/0197564 A1 | 9/2005 | Dempsey |
| 2005/0201509 A1 | 9/2005 | Mostafavi et al. |
| 2005/0201510 A1 | 9/2005 | Mostafavi |
| 2005/0213705 A1 | 9/2005 | Hoffman |

(56) References Cited

U.S. PATENT DOCUMENTS

| | | |
|---|---|---|
| 2005/0228255 A1 | 10/2005 | Saracen et al. |
| 2005/0234327 A1 | 10/2005 | Saracen et al. |
| 2006/0002511 A1 | 1/2006 | Miller et al. |
| 2006/0072699 A1 | 4/2006 | Mackie et al. |
| 2006/0113482 A1 | 6/2006 | Pelizzari et al. |
| 2006/0124854 A1 | 6/2006 | Shah |
| 2006/0173294 A1 | 8/2006 | Ein-Gal |
| 2006/0182326 A1 | 8/2006 | Schildkraut et al. |
| 2006/0193435 A1 | 8/2006 | Hara et al. |
| 2006/0193441 A1 | 8/2006 | Cadman |
| 2006/0237652 A1 | 10/2006 | Kimchy et al. |
| 2007/0003010 A1 | 1/2007 | Guertin et al. |
| 2007/0003123 A1 | 1/2007 | Fu et al. |
| 2007/0014391 A1 | 1/2007 | Mostafavi et al. |
| 2007/0023669 A1 | 2/2007 | Hefetz et al. |
| 2007/0025496 A1 | 2/2007 | Brown et al. |
| 2007/0025513 A1 | 2/2007 | Ghelmansarai |
| 2007/0043289 A1 | 2/2007 | Adair |
| 2007/0053491 A1 | 3/2007 | Schildkraut et al. |
| 2007/0055144 A1 | 3/2007 | Neustadter et al. |
| 2007/0133749 A1 | 6/2007 | Mazin et al. |
| 2007/0153969 A1 | 7/2007 | Maschke |
| 2007/0164239 A1 | 7/2007 | Terwilliger et al. |
| 2007/0165779 A1 | 7/2007 | Chen et al. |
| 2007/0167801 A1 | 7/2007 | Webler et al. |
| 2007/0211857 A1 | 9/2007 | Urano et al. |
| 2007/0221869 A1 | 9/2007 | Song |
| 2007/0237290 A1 | 10/2007 | Mostafavi |
| 2007/0265528 A1 | 11/2007 | Xu et al. |
| 2007/0270693 A1 | 11/2007 | Fiedler et al. |
| 2008/0002811 A1 | 1/2008 | Allison |
| 2008/0031404 A1 | 2/2008 | Khamene et al. |
| 2008/0043910 A1 | 2/2008 | Thomas |
| 2008/0095416 A1 | 4/2008 | Jeung et al. |
| 2008/0103391 A1 | 5/2008 | Dos Santos Varela |
| 2008/0128631 A1 | 6/2008 | Suhami |
| 2008/0130825 A1 | 6/2008 | Fu et al. |
| 2008/0152085 A1 | 6/2008 | Saracen et al. |
| 2008/0156993 A1 | 7/2008 | Weinberg et al. |
| 2008/0164875 A1 | 7/2008 | Haworth et al. |
| 2008/0203309 A1 | 8/2008 | Frach et al. |
| 2008/0205588 A1 | 8/2008 | Kim |
| 2008/0214927 A1 | 9/2008 | Cherry et al. |
| 2008/0217541 A1 | 9/2008 | Kim |
| 2008/0230705 A1 | 9/2008 | Rousso et al. |
| 2008/0251709 A1 | 10/2008 | Cooke et al. |
| 2008/0253516 A1 | 10/2008 | Hui et al. |
| 2008/0262473 A1 | 10/2008 | Kornblau et al. |
| 2008/0272284 A1 | 11/2008 | Rietzel |
| 2008/0273659 A1 | 11/2008 | Guertin et al. |
| 2008/0298536 A1 | 12/2008 | Ein-Gal |
| 2009/0003655 A1 | 1/2009 | Wollenweber |
| 2009/0086909 A1 | 4/2009 | Hui et al. |
| 2009/0088622 A1 | 4/2009 | Mostafavi |
| 2009/0116616 A1 | 5/2009 | Lu et al. |
| 2009/0131734 A1 | 5/2009 | Neustadter et al. |
| 2009/0169082 A1 | 7/2009 | Mizuta et al. |
| 2009/0236532 A1 | 9/2009 | Frach et al. |
| 2009/0256078 A1 | 10/2009 | Mazin |
| 2009/0309046 A1 | 12/2009 | Balakin |
| 2010/0010343 A1 | 1/2010 | Daghighian et al. |
| 2010/0040197 A1 | 2/2010 | Maniawski et al. |
| 2010/0049030 A1 | 2/2010 | Saunders et al. |
| 2010/0054408 A1 | 3/2010 | Echner |
| 2010/0054412 A1 | 3/2010 | Brinks et al. |
| 2010/0063384 A1 | 3/2010 | Kornblau et al. |
| 2010/0065723 A1 | 3/2010 | Burbar et al. |
| 2010/0067660 A1 | 3/2010 | Maurer, Jr. et al. |
| 2010/0069742 A1 | 3/2010 | Partain et al. |
| 2010/0074400 A1 | 3/2010 | Sendai |
| 2010/0074498 A1 | 3/2010 | Breeding et al. |
| 2010/0166274 A1 | 7/2010 | Busch et al. |
| 2010/0176309 A1 | 7/2010 | Mackie et al. |
| 2010/0198063 A1 | 8/2010 | Huber et al. |
| 2010/0237259 A1 | 9/2010 | Wang |
| 2010/0266099 A1 | 10/2010 | Busch et al. |
| 2010/0276601 A1 | 11/2010 | Duraj et al. |
| 2011/0006212 A1 | 1/2011 | Shchory et al. |
| 2011/0044429 A1 | 2/2011 | Takahashi et al. |
| 2011/0073763 A1 | 3/2011 | Subbarao |
| 2011/0092814 A1 | 4/2011 | Yamaya et al. |
| 2011/0105895 A1 | 5/2011 | Kornblau et al. |
| 2011/0105897 A1 | 5/2011 | Kornblau et al. |
| 2011/0118588 A1 | 5/2011 | Kornblau et al. |
| 2011/0198504 A1 | 8/2011 | Eigen |
| 2011/0200170 A1 | 8/2011 | Nord et al. |
| 2011/0210261 A1 | 9/2011 | Maurer, Jr. |
| 2011/0211665 A1 | 9/2011 | Maurer, Jr. et al. |
| 2011/0215248 A1 | 9/2011 | Lewellen et al. |
| 2011/0215259 A1 | 9/2011 | Iwata |
| 2011/0272600 A1 | 11/2011 | Bert et al. |
| 2011/0297833 A1 | 12/2011 | Takayama |
| 2011/0301449 A1 | 12/2011 | Maurer, Jr. |
| 2011/0309252 A1 | 12/2011 | Moriyasu et al. |
| 2011/0309255 A1 | 12/2011 | Bert et al. |
| 2011/0313231 A1 | 12/2011 | Guertin et al. |
| 2011/0313232 A1 | 12/2011 | Balakin |
| 2012/0035470 A1 | 2/2012 | Kuduvalli et al. |
| 2012/0068076 A1 | 3/2012 | Daghighian |
| 2012/0076269 A1 | 3/2012 | Roberts |
| 2012/0138806 A1 | 6/2012 | Holmes et al. |
| 2012/0161014 A1 | 6/2012 | Yamaya et al. |
| 2012/0174317 A1 | 7/2012 | Saracen et al. |
| 2012/0189102 A1 | 7/2012 | Maurer, Jr. et al. |
| 2012/0203490 A1 | 8/2012 | Sayeh et al. |
| 2012/0213334 A1 | 8/2012 | Dirauf et al. |
| 2012/0230464 A1 | 9/2012 | Ling et al. |
| 2012/0318989 A1 | 12/2012 | Park et al. |
| 2012/0323117 A1 | 12/2012 | Neustadter et al. |
| 2013/0025055 A1 | 1/2013 | Saracen et al. |
| 2013/0060134 A1 | 3/2013 | Eshima et al. |
| 2013/0092842 A1 | 4/2013 | Zhang et al. |
| 2013/0109904 A1 | 5/2013 | Siljamaki et al. |
| 2013/0111668 A1 | 5/2013 | Wiggers et al. |
| 2013/0193330 A1 | 8/2013 | Wagadarikar et al. |
| 2013/0266116 A1 | 10/2013 | Abenaim et al. |
| 2013/0279658 A1 | 10/2013 | Mazin |
| 2013/0327932 A1 | 12/2013 | Kim et al. |
| 2013/0343509 A1 | 12/2013 | Gregerson et al. |
| 2014/0029715 A1 | 1/2014 | Hansen et al. |
| 2014/0079179 A1 | 3/2014 | Takagaki et al. |
| 2014/0104051 A1 | 4/2014 | Breed |
| 2014/0107390 A1 | 4/2014 | Brown et al. |
| 2014/0110573 A1 | 4/2014 | Wang et al. |
| 2014/0163368 A1 | 6/2014 | Rousso et al. |
| 2014/0184197 A1 | 7/2014 | Dolinsky |
| 2014/0193336 A1 | 7/2014 | Rousso et al. |
| 2014/0217294 A1 | 8/2014 | Rothfuss et al. |
| 2014/0224963 A1 | 8/2014 | Guo et al. |
| 2014/0228613 A1 | 8/2014 | Mazin et al. |
| 2014/0239204 A1 | 8/2014 | Orton et al. |
| 2014/0257096 A1 | 9/2014 | Prevrhal et al. |
| 2014/0341351 A1 | 11/2014 | Berwick et al. |
| 2014/0355735 A1 | 12/2014 | Choi et al. |
| 2014/0371581 A1 | 12/2014 | Mostafavi et al. |
| 2015/0018673 A1 | 1/2015 | Rose et al. |
| 2015/0035942 A1 | 2/2015 | Hampton et al. |
| 2015/0076357 A1 | 3/2015 | Frach |
| 2015/0078528 A1 | 3/2015 | Okada |
| 2015/0126801 A1 | 5/2015 | Matteo et al. |
| 2015/0131774 A1 | 5/2015 | Maurer, Jr. et al. |
| 2015/0131781 A1 | 5/2015 | Ohashi et al. |
| 2015/0150740 A1 | 6/2015 | Lewald et al. |
| 2015/0168567 A1 | 6/2015 | Kim et al. |
| 2015/0170778 A1 | 6/2015 | Echner et al. |
| 2015/0177394 A1 | 6/2015 | Dolinsky et al. |
| 2015/0190658 A1 | 7/2015 | Yu |
| 2015/0276947 A1 | 10/2015 | Hoenk et al. |
| 2015/0285922 A1 | 10/2015 | Mintzer et al. |
| 2015/0301201 A1 | 10/2015 | Rothfuss et al. |
| 2016/0023019 A1 | 1/2016 | Filiberti et al. |
| 2016/0073977 A1 | 3/2016 | Mazin |
| 2016/0097866 A1 | 4/2016 | Williams |
| 2016/0146949 A1 | 5/2016 | Frach et al. |

(56) References Cited

U.S. PATENT DOCUMENTS

| | | |
|---|---|---|
| 2016/0155228 A1 | 6/2016 | Sakata et al. |
| 2016/0206203 A1 | 7/2016 | Yu et al. |
| 2016/0209515 A1 | 7/2016 | Da Silva Rodrigues et al. |
| 2016/0219686 A1 | 7/2016 | Nakayama et al. |
| 2016/0266260 A1 | 9/2016 | Preston |
| 2016/0273958 A1 | 9/2016 | Hoenk et al. |
| 2016/0287347 A1 | 10/2016 | Meier |
| 2016/0299240 A1 | 10/2016 | Cho et al. |
| 2016/0325117 A1 | 11/2016 | Arai |
| 2016/0361566 A1 | 12/2016 | Larkin et al. |
| 2016/0374632 A1 | 12/2016 | David |
| 2017/0014648 A1 | 1/2017 | Mostafavi |
| 2017/0036039 A1 | 2/2017 | Gaudio |
| 2017/0052266 A1 | 2/2017 | Kim et al. |
| 2017/0065834 A1 | 3/2017 | Liu |
| 2017/0082759 A1 | 3/2017 | Lyu et al. |
| 2017/0199284 A1 | 7/2017 | Silari et al. |
| 2017/0220709 A1 | 8/2017 | Wan et al. |
| 2017/0242136 A1 | 8/2017 | O'Neill et al. |
| 2017/0281975 A1 | 10/2017 | Filiberti et al. |
| 2018/0133508 A1 | 5/2018 | Pearce et al. |
| 2018/0292550 A1 | 10/2018 | Xu et al. |
| 2019/0070437 A1 | 3/2019 | Olcott et al. |
| 2019/0126069 A1 | 5/2019 | Nord et al. |
| 2019/0357859 A1 | 11/2019 | Mazin |
| 2020/0215355 A1 | 7/2020 | Olcott et al. |
| 2020/0368557 A1 | 11/2020 | Harper et al. |
| 2021/0196212 A1 | 7/2021 | Mazin |
| 2021/0327560 A1 | 10/2021 | Carmi |
| 2022/0342095 A1 | 10/2022 | Olcott et al. |
| 2023/0337991 A1 | 10/2023 | Mazin |
| 2023/0393292 A1 | 12/2023 | Olcott et al. |

FOREIGN PATENT DOCUMENTS

| | | | |
|---|---|---|---|
| CN | 1960780 A | 5/2007 | |
| CN | 101297759 A | 11/2008 | |
| CN | 101378805 A | 3/2009 | |
| CN | 101803929 A | 8/2010 | |
| CN | 101970043 A | 2/2011 | |
| CN | 103071241 A | 5/2013 | |
| CN | 103648392 A | 3/2014 | |
| CN | 103650095 A | 3/2014 | |
| CN | 103932789 A | 7/2014 | |
| CN | 105073188 A | 11/2015 | |
| CN | 106461801 A | 2/2017 | |
| DE | 10-2008-053321 A1 | 5/2010 | |
| DE | 10-2013-205606 A1 | 10/2014 | |
| EP | 0 437 434 A1 | 7/1995 | |
| EP | 0 817 978 A1 | 8/2001 | |
| EP | 0 984 393 B1 | 3/2007 | |
| EP | 1 762 177 A2 | 3/2007 | |
| EP | 1 501 604 B1 | 12/2009 | |
| EP | 1 898 234 B1 | 4/2010 | |
| EP | 2 188 815 B1 | 11/2011 | |
| EP | 2 687 259 A1 | 1/2014 | |
| EP | 2 872 913 B1 | 2/2016 | |
| EP | 2 874 702 B1 | 9/2016 | |
| EP | 1 664 752 B1 | 6/2017 | |
| FR | 2839894 A1 | 11/2003 | |
| GB | 69634119 T2 | 2/2006 | |
| GB | 2513596 A | 11/2014 | |
| IL | 208396 | 12/2010 | |
| JP | H-01-156830 A | 6/1989 | |
| JP | 09-33658 A | 2/1997 | |
| JP | H-09-122110 A | 5/1997 | |
| JP | 9-189769 A2 | 7/1997 | |
| JP | H-11-290466 A | 10/1999 | |
| JP | 2000-105279 A | 4/2000 | |
| JP | 2001-340474 A | 12/2001 | |
| JP | 2002-263090 A | 9/2002 | |
| JP | 2003-534823 A | 11/2003 | |
| JP | 2004-073404 A | 3/2004 | |
| JP | 2004-513735 A | 5/2004 | |
| JP | 2005-261941 A | 9/2005 | |
| JP | 2006-145281 A | 6/2006 | |
| JP | 2007-502166 A | 2/2007 | |
| JP | 2007-507246 A | 3/2007 | |
| JP | 2008107326 A * | 5/2008 | ........... G01T 1/2018 |
| JP | 2008-173184 A | 7/2008 | |
| JP | 2008-173299 A | 7/2008 | |
| JP | 2009-544101 A | 12/2009 | |
| JP | 2010-500910 A | 1/2010 | |
| JP | 2010-517655 A | 5/2010 | |
| JP | 2011-007614 A | 1/2011 | |
| JP | 2011-508654 A | 3/2011 | |
| JP | 2011-514213 A | 5/2011 | |
| JP | 2012-042344 A | 3/2012 | |
| JP | 2012-129984 A | 7/2012 | |
| JP | 2012-254146 A | 12/2012 | |
| JP | 2013-257320 A | 12/2013 | |
| JP | 2013-545560 A | 12/2013 | |
| JP | 2014-521370 A | 8/2014 | |
| JP | 2017-199876 A | 11/2017 | |
| NL | 9520013 A | 2/1997 | |
| WO | WO-89/10090 A1 | 11/1989 | |
| WO | WO-95/22241 A1 | 8/1995 | |
| WO | WO-00/15299 A1 | 3/2000 | |
| WO | WO-2004/017832 A2 | 3/2004 | |
| WO | WO-2004/017832 A3 | 3/2004 | |
| WO | WO-2005/018734 A2 | 3/2005 | |
| WO | WO-2005/018734 A3 | 3/2005 | |
| WO | WO-2005/018735 A2 | 3/2005 | |
| WO | WO-2005/018735 A3 | 3/2005 | |
| WO | WO-2005/110495 A1 | 11/2005 | |
| WO | WO-2006/051531 A2 | 5/2006 | |
| WO | WO-2006/051531 A3 | 5/2006 | |
| WO | WO-2006/086765 A2 | 8/2006 | |
| WO | WO-2006/086765 A3 | 8/2006 | |
| WO | WO-2007/045076 A1 | 4/2007 | |
| WO | WO-2007/094002 A2 | 8/2007 | |
| WO | WO-2007/094002 A3 | 8/2007 | |
| WO | WO-2007/120674 A2 | 10/2007 | |
| WO | WO-2007/120674 A3 | 10/2007 | |
| WO | WO-2007/124760 A1 | 11/2007 | |
| WO | WO-2008/019118 A2 | 2/2008 | |
| WO | WO-2008/019118 A3 | 2/2008 | |
| WO | WO-2008/024463 A2 | 2/2008 | |
| WO | WO-2008/024463 A3 | 2/2008 | |
| WO | WO-2008/127368 A2 | 10/2008 | |
| WO | WO-2008/127368 A3 | 10/2008 | |
| WO | WO-2009/111580 A2 | 9/2009 | |
| WO | WO-2009/111580 A3 | 9/2009 | |
| WO | WO-2009/114117 A2 | 9/2009 | |
| WO | WO-2009/114117 A3 | 9/2009 | |
| WO | WO-2010/015358 A1 | 2/2010 | |
| WO | WO-2010/018477 A2 | 2/2010 | |
| WO | WO-2010/018477 A3 | 2/2010 | |
| WO | WO-2010/109585 A1 | 9/2010 | |
| WO | WO-2010/110255 A1 | 9/2010 | |
| WO | WO-2012/135771 A1 | 10/2012 | |
| WO | WO-2013/168043 A2 | 11/2013 | |
| WO | WO-2013/168043 A3 | 11/2013 | |
| WO | WO-2015/038832 A1 | 3/2015 | |
| WO | WO-2015/042510 A1 | 3/2015 | |
| WO | WO-2015/103564 A1 | 7/2015 | |
| WO | WO-2015/134953 A1 | 9/2015 | |
| WO | WO-2015/161036 A1 | 10/2015 | |
| WO | WO-2016/097977 A1 | 6/2016 | |
| WO | WO-2016/203822 A1 | 12/2016 | |

OTHER PUBLICATIONS

Chang, J.Y. et al. (2008). "Image-guided radiation therapy for non-small cell lung cancer," *J. Thorac. Oncol.* 3(2):177-186.

Chen, Y. et al. (2011). Dynamic tomotherapy delivery, *Am. Assoc. Phys. Med.* 38:3013-3024.

Corrected Notice of Allowability mailed on Jan. 29, 2020, for U.S. Appl. No. 16/100,054, filed Aug. 9, 2018, 4 pages.

Corrected Notice of Allowability mailed on Feb. 3, 2021, for U.S. Appl. No. 16/425,416, filed May 29, 2019, 2 pages.

Corrected Notice of Allowability mailed on Feb. 14, 2023, for U.S. Appl. No. 17/697,828, filed Mar. 17, 2022, 4 pages.

(56) References Cited

OTHER PUBLICATIONS

Corrected Notice of Allowability mailed on Feb. 23, 2023, for U.S. Appl. No. 17/697,828, filed Mar. 17, 2022, 2 pages.
Corrected Notice of Allowability mailed on Mar. 16, 2023, for U.S. Appl. No. 17/203,532, filed Mar. 16, 2021, 2 pages.
Dieterich, S. et al. (2003). "Skin respiratory motion tracking for stereotactic radiosurgery using the CyberKnife," *Elsevier Int'l Congress Series* 1256:130-136.
Erdi, Y.E. (2007). "The use of PET for radiotherapy," *Curr. Medical Imaging Reviews* 3(1):3-16.
Extended European Search Report mailed on Mar. 31, 2017, for European Application No. 09 719 473.2, filed on Mar. 9, 2009, 8 pages.
Extended European Search Report mailed on Jun. 9, 2020, for EP Application No. 17 871 349.1, filed on Nov. 15, 2017, 6 pages.
Extended European Search Report mailed on Oct. 30, 2020, for EP Application No. 20 179 036.7, filed on Mar. 9, 2009, 12 pages.
Extended European Search Report mailed on Apr. 1, 2021, for EP Application No. 18 844 237.0, filed on Aug. 9, 2018, 8 pages.
Extended European Search Report mailed on May 26, 2021, for EP Application No. 18 832 571.6, filed on Jul. 11, 2018, 9 pages.
Extended European Search Report mailed on Mar. 30, 2022, for EP Application No. 21 195 331.0, filed on Nov. 15, 2017, 11 pages.
Fan, Q. et al. (2012). "Emission Guided Radiation Therapy for Lung and Prostrate Cancers: A Feasibility Study on a Digital Patient," *Med. Phys.* 39(11):7140-7152.
Fan, Q. et al. (2013). "Toward a Planning Scheme for Emission Guided Radiation Therapy (EGRT): FDG Based Tumor Tracking in a Metastatic Breast Cancer Patient," *Med. Phys.* 40(8): 12 pages.
Final Office Action mailed on Aug. 15, 2012, for U.S. Appl. No. 13/209,275, filed Aug. 12, 2011, 8 pages.
Final Office Action mailed on Aug. 10, 2021, for U.S. Appl. No. 16/887,896, filed May 29, 2020, 66 pages.
Galvin, J.M. (2018). "The multileaf collimator—A complete guide," 17 total pages.
Gibbons, J.P. (2004). "Dose calculation and verification for tomotherapy," 2004 ACMP Meeting, Scottsdale, AZ., 71 total pages.
Glendinning, A.G. et al. (2001). "Measurement of the response of $Gd_2O_2S$:Tb phosphor to 6 MV x-rays," Phys. Mol. Biol. 46:517-530.
Handsfield, L.L. et al. (2014). "Phantomless patient-specific TomoTherapy QA via delivery performance monitoring and a secondary Monte Carlo dose calculation," *Med. Phys.* 41:101703-1-101703-9.
International Search Report mailed on May 4, 2009, for PCT Application No. PCT/US2009/01500, filed on Mar. 9, 2009, 3 pages.
International Search Report mailed on Mar. 7, 2018, for PCT Application No. PCT/US2017/061848, filed on Nov. 15, 2017, 4 pages.
International Search Report mailed on Oct. 2, 2018, for PCT Application No. PCT/US2018/041700, filed on Jul. 11, 2018, 2 pages.
International Search Report mailed on Oct. 24, 2018, for PCT Application No. PCT/US2018/046132, filed on Aug. 9, 2018, 2 pages.
International Search Report mailed on Mar. 13, 2018, for PCT Application No. PCT/US2017/061855, filed on Nov. 15, 2017, 4 pages.
Kapatoes, J.M. et al. (2001). "A feasible method for clinical delivery verification and dose reconstruction in tomotherapy," *Med. Phys.* 28:528-542.
Keall, P.J. et al. (2001). "Motion adaptive x-ray therapy: a feasibility study," *Phys. Med. Biol.* 46:1-10.
Kim, H. et al. (2009). "A multi-threshold method for the TOF-PET Signal Processing," Nucl. Instrum. Meth. Phys. Res. A. 602:618-621.
Krouglicof, N. et al. (2013). "Development of a Novel PCB-Based Voice Coil Actuator for Opto-Mechatronic Applications," presented at *IEEE/RSJ International Conference on Intelligent Robots and Systems* (*IROS*), Tokyo, Japan, Nov. 3-7, 2013, pp. 5834-5840.
Langen, K.M. et al. (2010). "QA for helical tomotherapy: report of the AAPM Task Group 148," *Med. Phys.* 37:4817-4853.
Li, X. et al. (2016). "Timing calibration for Time-of-Flight PET using positron-emitting isotopes and annihilation targets," IEEE Transactions on Nuclear Science 63:1351-1358.
Lu, W. (2009). "Real-time motion-adaptive-optimization (MAO) in tomotherapy," Phys. Med. Biol. 54:4373-4398.
Lu, W. (2008). "Real-time motion-adaptive delivery (MAD) using binary MLC: I. Static beam (topotherapy) delivery," Phys. Med. Biol. 53:6491-6511.
Mackie, T.R. et al. (Nov.-Dec. 1993). "Tomotherapy: A New Concept for the Delivery of Dynamic Conformal Radiotherapy," *Med. Phys.* 20(6):1709-1719.
McMahon, R. et al. (2008). "A real-time dynamic-MLC control algorithm for delivering IMRT to targets undergoing 2D rigid motion in the beam's eye view," Med. Phys. 35:3875-3888.
Mazin, S. R. et al. (2010). "Emission-Guided Radiation Therapy: Biologic Targeting and Adaptive Treatment," *Journal of American College of Radiology* 7(12):989-990.
Non-Final Office Action mailed on Jan. 10, 2011, for U.S. Appl. No. 12/367,679, filed Feb. 9, 2009, 9 pages.
Non-Final Office Action mailed on Feb. 28, 2012, for U.S. Appl. No. 13/209,275, filed Aug. 12, 2011, 8 pages.
Non-Final Office Action mailed on Sep. 19, 2013, for U.S. Appl. No. 13/895,255, filed May 15, 2013, 8 pages.
Non-Final Office Action mailed on Jan. 7, 2020, for U.S. Appl. No. 15/814,222, filed Nov. 15, 2017, 13 pages.
Non-Final Office Action mailed on Oct. 5, 2020, for U.S. Appl. No. 16/887,896, filed May 29, 2020, 62 pages.
Non-Final Office Action mailed on Nov. 3, 2020, for U.S. Appl. No. 16/818,325, filed Mar. 13, 2020, 9 pages.
Non-Final Office Action mailed on Mar. 12, 2021, for U.S. Appl. No. 16/887,896, filed May 29, 2020, 64 pages.
Non-Final Office Action mailed on Jul. 5, 2022, for U.S. Appl. No. 17/203,532, filed Mar. 16, 2021, 13 pages.
Non-Final Office Action mailed on Dec. 14, 2022, for U.S. Appl. No. 16/887,852, filed May 29, 2020, 12 pages.
Non-Final Office Action mailed on Jan. 17, 2023, for U.S. Appl. No. 17/837,900, filed Jun. 10, 2022, 12 pages.
Non-Final Office Action mailed on Jan. 20, 2023, for U.S. Appl. No. 17/852,067, filed Jun. 28, 2022, 21 pages.
Non-Final Office Action mailed on Jan. 27, 2023, for U.S. Appl. No. 17/485,059, filed Sep. 24, 2021, 11 pages.
Notice of Allowance mailed on Jul. 25, 2011, for U.S. Appl. No. 12/367,679, filed Feb. 9, 2009, 7 pages.
Notice of Allowance mailed on Apr. 9, 2014, for U.S. Appl. No. 13/895,255, filed May 15, 2013, 7 pages.
Notice of Allowance mailed on Oct. 27, 2015, for U.S. Appl. No. 14/278,973, filed May 15, 2014, 8 pages.
Notice of Allowance mailed on Mar. 27, 2013, for U.S. Appl. No. 13/209,275, filed Aug. 12, 2011, 9 pages.
Notice of Allowance mailed on Oct. 5, 2017, for U.S. Appl. No. 14/951,194, filed Nov. 24, 2015, 11 pages.
Notice of Allowance mailed on Apr. 4, 2019, for U.S. Appl. No. 15/807,383, filed Nov. 8, 2017, 11 pages.
Notice of Allowance mailed on Dec. 4, 2019, for U.S. Appl. No. 16/100,054, filed Aug. 9, 2018, 13 pages.
Notice of Allowance mailed on Apr. 10, 2020, for U.S. Appl. No. 16/033,125, filed Jul. 11, 2018, 18 pages.
Notice of Allowance mailed on Apr. 30, 2020, for U.S. Appl. No. 15/814,222, filed Nov. 15, 2017, 10 pages.
Notice of Allowance mailed on Jan. 12, 2021, for U.S. Appl. No. 16/425,416, filed May 29, 2019, 13 pages.
Notice of Allowance mailed on Feb. 22, 2021, for U.S. Appl. No. 16/818,325, filed Mar. 13, 2020, 7 pages.
Notice of Allowance mailed on Dec. 22, 2021, for U.S. Appl. No. 16/887,896, filed May 29, 2020, 11 pages.
Notice of Allowance mailed on Jul. 12, 2022, for U.S. Appl. No. 17/238,113, filed Apr. 22, 2021, 9 pages.
Notice of Allowance mailed on Aug. 1, 2022, for U.S. Appl. No. 17/238,113, filed Apr. 22, 2021, 8 pages.

(56) References Cited

OTHER PUBLICATIONS

Notice of Allowance mailed on Dec. 15, 2022, for U.S. Appl. No. 17/203,532, filed Mar. 16, 2021, 8 pages.
Notice of Allowance mailed on Feb. 7, 2023, for U.S. Appl. No. 17/697,828, filed Mar. 17, 2022, 10 pages.
North Shore LIJ (2008). IMRT treatment plans: Dosimetry measurements & monitor units validation, 133 total pages.
Olivera, G.H. et al. (2000). "Modifying a plan delivery without re-optimization to account for patient offset in tomotherapy," Proceedings of the 22$^{nd}$ Annual EMBS International Conference, Jul. 23-28, 2000, Chicago, IL, pp. 441-444.
Papanikolaou, N. et al. (2010). "MU-Tomo: Independent dose validation software for helical tomo therapy," *J. Cancer Sci. Ther.* 2:145-152.
Parodi, K. (2015). "Vision 20/20: Positron emission tomography in radiation therapy planning, delivery, and monitoring," *Med. Phys.* 42:7153-7168.
Prabhakar, R. et al. (2007). "An Insight into PET-CT Based Radiotherapy Treatment Planning," *Cancer Therapy* (5):519-524.
Schleifring (2013). Slip Ring Solutions—Technology, 8 total pages.
Tashima, H. et al. (2012). "A Single-Ring Open PET Enabling PET Imaging During Radiotherapy," *Phys. Med. Biol.* 57(14):4705-4718.
TomoTherapy® (2011). TOMOHD Treatment System, Product Specifications, 12 total pages.
Varian Medical Systems (2004). "Dynamic Targeting™ Image-Guided Radiation Therapy—A Revolution in Cancer Care," *Business Briefing: US Oncology Review*, Abstract only, 2 pages.
ViewRay's MRIDIAN LINAC enables radiosurgery with MRI vision for cancer therapy, (2017). YouTube video located at https://www.youtube.com/watch?v=zm3g-BISYDQ, PDF of Video Screenshot Provided.
Wang, D. et al. (2006). "Initial experience of FDG-PET/CT guided IMRT of head-and-neck carcinoma," Int. J. Radiation Oncology Biol. Phys. 65:143-151.
Wikipedia (2016). "Scotch yoke," Retrieved from https://en.wikipedia.org/wiki/Scotch_yoke, 3 pages.
Willoughby, T. et al. (2012). "Quality assurance for nonradiographic radiotherapy localization and positioning systems: Report of task group 147," Med. Phys. 39:1728-1747.
Written Opinion of the International Searching Authority mailed on May 4, 2009, for PCT Application No. PCT/US2009/01500, filed on Mar. 9, 2009, 5 pages.
Written Opinion of the International Searching Authority mailed on Mar. 7, 2018, for PCT Application No. PCT/US2017/061848, filed on Nov. 15, 2017, 5 pages.
Written Opinion of the International Searching Authority mailed on Oct. 2, 2018, for PCT Application No. PCT/US2018/041700, filed on Jul. 11, 2018, 19 pages.
Written Opinion of the International Searching Authority mailed on Oct. 24, 2018, for PCT Application No. PCT/US2018/046132, filed on Aug. 9, 2018, 7 pages.
Yamaya, T. et al. (2008). "A proposal of an open PET geometry," *Physics in Med. and Biology* 53:757-773.
Corrected Notice of Allowability mailed on Jan. 30, 2024, for U.S. Appl. No. 16/887,852, filed May 29, 2020, 2 pages.
Extended European Search Report mailed on Jan. 24, 2024, for EP Application No. 23 160 060.2, filed on Mar. 9, 2009, 12 pages.
Non-Final Office Action mailed on Jan. 16, 2024, for U.S. Appl. No. 18/178,431, filed Mar. 3, 2023, 16 pages.
Notice of Allowance mailed on Dec. 28, 2023, for U.S. Appl. No. 16/887,852, filed May 29, 2020, 9 pages.
Notice of Allowance mailed on Feb. 7, 2024, for U.S. Appl. No. 18/311,134, filed May 2, 2023, 11 pages.

* cited by examiner

SYSTEMS AND METHODS FOR FAULT DETECTION IN EMISSION-GUIDED RADIOTHERAPY

CROSS-REFERENCE TO RELATED APPLICATIONS

This application is a continuation of U.S. patent application Ser. No. 17/238,113, filed Apr. 22, 2021, which is a continuation of U.S. patent application Ser. No. 16/818,325, filed Mar. 13, 2020, which is a continuation of U.S. patent application Ser. No. 16/100,054, filed Aug. 9, 2018, now issued U.S. Pat. No. 10,603,515, which claims priority to U.S. Provisional Patent Application No. 62/543,140, filed Aug. 9, 2017, each of which is hereby incorporated by reference in its entirety.

FIELD

Systems and methods herein relate to patient imaging, which may be used in diagnostic and/or therapeutic applications, including but not limited to quality control procedures and fault detection for positron emission tomography (PET) systems.

BACKGROUND

Positron emission tomography (PET) is a non-invasive imaging technique that detects positron annihilation events (e.g., coincidence or coincident photon events) along a line of response (LOR) using opposing PET detectors. Time of flight (TOF) PET measures a time difference of coincidence events at the PET detectors to determine a corresponding annihilation location along the LOR. Determination of an annihilation location within a predetermined margin of error is dependent on proper calibration of the detector's time resolution. PET systems, including TOF PET systems, commonly undergo a daily quality assurance (QA) procedure to verify a time calibration of the PET detectors. For diagnostic imaging, a loss of calibration between QA checks may generate inaccurate patient data and require the patient to repeat an imaging session.

In some applications, emission-guided radiation therapy (EGRT) uses an array of PET detectors to provide real-time location data of positron emissions originating from a patient tumor and a radiation source to therapeutically irradiate the tumor based on the location data. A loss of calibration of the PET detectors during an EGRT treatment session (e.g., between QA checks) and/or any degradation in the spatial resolution, temporal resolution, energy sensitivity and/or precision, as well as the inability to precisely determine the location of a patient tumor region relative to the therapeutic radiation source may lead to suboptimal radiation therapy treatment and damage to healthy tissue. Therefore, it may be desirable to provide real-time fault detection in a TOF PET system that may more quickly identify a time calibration error and/or faulty PET detectors.

BRIEF SUMMARY

Disclosed herein are systems and methods for emission-guided radiation therapy using one or more positron emission detectors (PET detectors). Generally, a calibration source may be used to monitor the operation of the one or more positron emission detectors. The calibration source may be a radiation source (e.g., radiation source generating positron annihilation events) that is distinct and spatially separated from radiation sources located within a patient (e.g., radiotracers and/or implanted fiducials) and may be held between a plurality of positron emission detectors while treating and/or imaging the patient. The detectors may concurrently receive positron emission data from the patient and calibration source. The positron emission data of the calibration source may be used to verify the functionality and/or precision of the positron emission detectors. Although the calibration source may be disposed near the patient, the calibration source may be of a size and radioactivity sufficient to be located by the detectors without significant risk to the patient.

In some variations, an imaging assembly is provided, comprising a gantry comprising a plurality of positron emission detectors and a housing comprising a calibration source holder such as a radiation source holder. The housing may be coupled to the gantry. The gantry may further comprise a bore and a patient scan or treatment region may be located within the bore and disposed between the positron emission detectors. The calibration source holder may be stationary and be spaced away from the patient scan or treatment region within the bore. The stationary calibration source holder may be located within the housing or on a surface of the housing. The positron emission detectors may comprise a first array of rotatable positron emission detectors and a second array of positron emission detectors. The assembly may further comprise a processor configured to receive positron emission data from the first and second arrays of rotatable positron emission detectors and to distinguish the positron emission data from the stationary calibration source holder and from the patient scan region, and to generate a fault signal when the positron emission data from the stationary calibration source holder exceeds a threshold parameter.

In some variations, the assembly may further comprise a patient support. The patient support may comprise a movable support surface and a base. In some of these variations, the calibration source holder may be disposed along the surface of the housing at a location above the patient scan region. In other of these variations, the calibration source holder may be located below the movable support surface. In some variations, a calibration source (e.g., radiation source) may be held by the calibration source holder. In some of these variations, the calibration source may comprise a radioactivity of about 1 µCi to 300 µCi, e.g., about 2 µCi, about 100 µCi, and an energy of about 511 keV. In other of these variations, the calibration source may comprise a shape with a maximum dimension from about 0.25 inch to about 3 inches, e.g., about 1 inch, about 2 inches. In another variation, the threshold parameter may be a variability threshold parameter. In yet another variation, the processor may be further configured to concurrently classify the positron emission data from the calibration source holder and from the patient scan region. In some variations, the processor may be configured with a spatial filter to distinguish the positron emission data from the stationary calibration source holder and from the patient scan region. In some of these variations, the spatial filter may be user adjustable. In other of these variations, the processor may be further configured to automatically adjust a geometry of the spatial filter using a patient treatment plan.

Also described here are other imaging assemblies. In some variations, an imaging assembly is provided, comprising a gantry comprising a plurality of positron emission detectors and a housing comprising a calibration source such as a radiation source. The housing may be disposed over the gantry. The gantry may further comprise a bore for a patient to be disposed between the positron emission detectors. The calibration source may be stationary and spaced away from a patient scan region within the bore. The calibration source may be located within the housing or on a surface of the housing. The positron emission detectors may comprise a first array of rotatable positron emission detectors and a second array of positron emission detectors opposing the first array of detectors. The assembly may further comprise a processor configured to receive positron emission path data from the first and second arrays of rotatable positron emission detectors and to classify positron emission path data that originates from the stationary calibration source, and to generate a fault signal when the stationary calibration source positron emission path data exceeds a threshold parameter.

In some variations, a pair of photons emitted by a positron annihilation event generates a positron emission path. The processor may be configured to classify the positron emission path data that originates from the stationary calibration source using a difference between a reception time of the pairs of photons within a time threshold parameter range. In some of these variations, the threshold parameter is a location deviation threshold. The processor may be configured to calculate the location of the stationary calibration source based on the reception time difference of the pairs of photons, and to generate the fault signal when the calculated location of the stationary calibration source exceeds the location deviation threshold. In other variations, the threshold parameter is a time difference range. The processor may be configured to generate the fault signal when a difference between a reception time of the pairs of photons is outside of the time difference range.

In some variations, an imaging assembly is provided, comprising a gantry comprising a plurality of positron emission detectors and a housing comprising an annular calibration source such as an annular radiation source. The housing may be coupled to the gantry. The housing may further comprise a bore and the annular calibration source may be about the bore. The positron emission detectors may comprise a first array of positron emission detectors and a second array of positron emission detectors opposing the first array of detectors. The assembly may further comprise a processor configured to receive positron emission data from the first and second arrays of positron emission detectors and to distinguish the positron emission data from the annular calibration source, and to generate a fault signal when the positron emission data from the annular calibration source exceeds a threshold parameter.

In some variations, the processor may be further configured to concurrently classify the positron emission data from the annular calibration source and from a patient scan region within the bore. In some of these variations, the processor may be further configured with a spatial filter to distinguish the positron emission data from the annular calibration source and from the patient scan region. In some variations, the first array and second array of detectors are stationary. In other variations, the first array and second array of detectors are rotatable.

In some variations, an imaging assembly is provided, comprising a gantry comprising a plurality of positron emission detectors. One or more calibration source holders may be coupled to the gantry such that the one or more calibration source holders are fixed relative to the positron emission detectors and configured to hold a radiation source. The plurality of positron emission detectors may comprise a first array of rotatable positron emission detectors and a second array of rotatable positron emission detectors opposing the first array of detectors. A processor may be configured to receive positron emission data from the first and second arrays of rotatable positron emission detectors and to distinguish the positron emission data from the one or more calibration source holders, and to generate a fault signal when the positron emission data from the one or more calibration source holders exceeds a threshold parameter.

In some of these variations, the gantry may comprise a bore. The bore may comprise a patient scan region spaced away from the one or more calibration source holders. The processor may be further configured to distinguish the positron emission data from the patient scan region in the bore. In some variations, one or more calibration source holders may comprise at least four calibration source holders. In another variation, one or more radiation sources may be held by the corresponding one or more calibration source holders. One or more radiation sources may comprise a radioactivity of about 1 µCi to 300 µCi, e.g., about 2 µCi, about 100 µCi. In some other variations, one or more calibration sources may comprise a shape selected from the group consisting of a cylinder, sphere, and ring.

Also described here are imaging methods. These methods may comprise the steps of receiving concurrent positron emission data from a patient and a calibration source spaced away from the patient, using a first array of positron emission detectors and a second array of positron emission detectors opposing the first array of detectors. The positron emission data may be distinguished from the patient and from the calibration source. Calibration data may be generated using the positron emission data from the calibration source. Patient data may be generated using the positron emission data from the patient. A fault signal may be generated when the calibration data exceeds a threshold parameter.

In some variations, the step of distinguishing the positron emission data from the patient and from the calibration source may comprise spatially filtering the positron emission data. In some of these variations, a spatial filter may be adjusted before applying the spatial filtering. For example, a spatial filter may be adjusted based on patient treatment plan parameters. In some of these variations, the spatial filtering of the positron emission data may comprise excluding the positron emission data located outside a calibration region and a patient region.

In other variations, receiving the positron emission data from the patient and the calibration source occurs concurrently with generating the fault signal. In another variation, the patient may be treated using a radiation source concurrently while receiving the positron emission data from the patient and from the calibration source. In some of these variations, treatment of the patient using the radiation source is stopped in response to generating the fault signal.

In other variations, one or more of the positron emission detectors may be deactivated based on the generation of the fault signal. In another variation, up to three of the first array and second array of detectors may be deactivated based on the generation of the fault signal. The fault signal may comprise a fault in up to three of the detectors. In yet another variation, all of the detectors may be deactivated based on the generation of the fault signal. The fault signal may comprise a fault in four or more of the detectors. In some variations, one or more of the positron emission detectors may be calibrated using the calibration data. In other variations, the positron emission data may correspond to lines of response non-intersecting with a patient imaging field of view of the detectors. The patient imaging field of view may comprise a patient scan region. In another variation, a fault detection system coupled to the detectors may be verified based on the generation of the fault signal.

One variation of a radiotherapy system (e.g., a radiation treatment assembly) may comprise a rotatable gantry, a first array of positron emission detectors mounted on the gantry and a second array of positron emission detectors mounted on the gantry opposite the first array of positron emission detectors, a therapeutic radiation source mounted on the rotatable gantry between the first and second arrays of positron emission detectors, a housing disposed over the rotatable gantry and comprising a bore and a stationary radiation source holder spaced away from a patient region within the bore, and a processor configured to receive positron emission data detected from the first and second arrays of positron emission detectors. The processor may be configured to extract positron emission data representing positron emission activity originating from the stationary radiation source holder, and to generate a fault signal when the extracted positron emission data does not satisfy one or more threshold criteria. The stationary radiation source holder may be located within the housing or on a surface of the housing. The system may further comprise a patient support, the patient support comprising a movable support surface and a base. The radiation source holder may be disposed along the surface of the housing at a location above the patient scan region, e.g., the radiation source holder may be located below the movable support surface. Some systems may further comprise a calibration radiation source held by the radiation source holder, the calibration source comprising a radioactivity of about 1 µCi to 300 µCi. The calibration radiation source may be configured to be retained by the radiation source holder, the calibration radiation source comprising a shape with a maximum dimension from about 0.25 inch to about 3 inches (e.g., 1 inch). The calibration radiation source may comprise a disk-shaped enclosure and a positron-emitting element located within the enclosure. The processor may be further configured to concurrently extract the positron emission data representing positron emission activity originating from the radiation source holder and to extract positron emission data representing positron emission activity originating from the patient scan region. A threshold criterion may comprise a spatial filter that selects for positron emission activity originating from a location of the stationary radiation source holder. A fault signal may be generated when applying the spatial filter to the extracted positron emission data indicates that the positron emission activity does not co-localize with the location of the stationary radiation source holder. the spatial filter may be user adjustable. Alternatively or additionally the processor may be further configured to automatically adjust a geometry of the spatial filter using a patient treatment plan.

In some variations, the first and second arrays of positron emission detectors may define an imaging plane, a beam of the therapeutic radiation source may define a treatment plane, and the imaging plane and the treatment plane may be co-planar. The stationary radiation source holder may be co-planar with the imaging plane and the treatment plane. In some variations, the stationary radiation source holder may comprise a groove having a shape that corresponds with a shape of the radiation source. In some variations, a threshold criterion may comprise a threshold number of coincident photon events detected with a first time difference (e.g., about 2.5 ns), and the processor may be configured to generate a plot of an actual number of coincident photon events detected with the time difference and a fault signal may be generated when the actual number of coincident photon events occurring with the time difference does not exceed the threshold number. A threshold positron emission detector criterion may comprise a threshold true-to-random ratio value, where the processor may be configured to generate a ratio of the actual number of coincident photon events occurring within a first coincidence time window (e.g., from −2.5 ns to +2.5 ns) centered around about 0 ns to an actual number of coincident photon events occurring within a second coincidence time window that does not overlap with the first coincidence time window (e.g., from 17.5 ns to 22.5 ns, not centered around 0 ns, having a similar window width as the first coincidence time window) and a fault signal may be generated if the ratio does not exceed the threshold true-to-random ratio value. In some variations, the threshold true-to-random ratio value may be 1 or more, e.g., about 1.1 or more, about 1.3 or more, about 1.5 or more, about 1.6 or more, about 2 or more, etc.

In some variations, a threshold criterion may comprise a first expected number of coincident photon events to be detected with a first detection time difference of about 2.5 ns at a first gantry location of the first array of positron emission detectors and a second expected number of coincident photon events to be detected with a detection time difference of about 2.5 ns at a second gantry location of the first array of the positron emission detectors that is 180° from the first gantry location. The processor may be configured to generate a plot of actual numbers of coincident photon events detected within a coincidence time window between −5 ns to +5 ns over a 360° gantry rotation based on positron emission data detected by the first and second arrays of positron emission detectors, and a fault signal may be generated when an actual number of coincident photon events detected with a detection time difference of about 2.5 ns at the first gantry location of the first array of the positron emission detectors does not meet or exceed the first expected number, and an actual number of coincident photon events detected with a detection time difference of about 2.5 ns at the second gantry location of the first array of the positron emission detectors does not meet or exceed the second expected number. Alternatively or additionally, a threshold criterion may comprise an expected number of coincident photon events to be detected by each positron emission detector of the first and second arrays at each gantry location over a 360° gantry rotation, and the processor may be configured to calculate, using the positron emission data detected by the first and second array of positron emission detectors, an actual number of coincident photon events detected by each positron emission detector of the first and second arrays at each gantry location over a 360° gantry rotation, and a fault signal may be generated when a difference between the actual number of coincident photon events and the expected number of coincident photon events exceeds a predetermined difference threshold for at least one positron emission detector. In some variations, a fault signal may be generated when the processor does not detect any positron emission data representing positron emission activity originating from the stationary radiation source holder. A threshold criterion comprises an energy resolution spectrum with a coincident 511 keV photon event count above a peak threshold, and a fault signal may be generated when an energy resolution spectrum generated from the positron emission data does not have a 511 keV photon event count above the peak threshold. Any of the systems described herein may comprise a display and the processor may be configured to generate a visual indicator and transmitting the visual indicator to the display. The visual indicator have a first appearance in the absence of a fault signal and a second appearance different from the first appearance when a fault signal is generated.

DETAILED DESCRIPTION

Figure 1A:
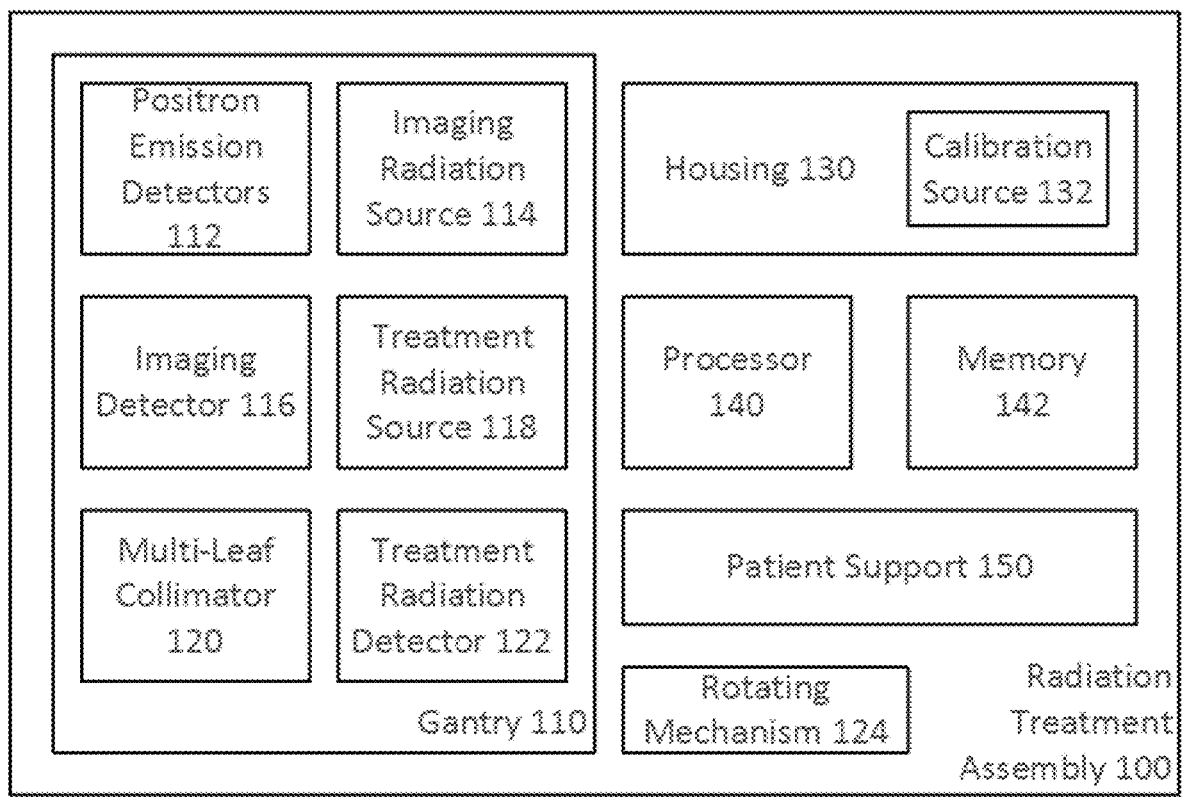
FIG. 1A is a block diagram of a variation of a radiation therapy assembly.

Described herein are radiation therapy and/or imaging systems and methods for monitoring PET detector parameters and quality metrics during a radiation therapy treatment session. These systems and methods may also be used for calibration separately from a treatment session. Conventional PET detector calibration monitoring is limited to time periods between patient radiation therapy treatment and/or imaging sessions. For example, a radiation point source at a known location on the system may be imaged by PET detectors on an empty couch for a QA procedure. After a QA procedure has been completed, a patient may be loaded onto the couch and undergo radiation therapy treatment and/or imaging. Conventional QA performed separately from a patient procedure reduces patient throughput and does not monitor the precision and/or accuracy of PET detectors during a radiation therapy treatment and/or imaging procedure.

Generally, the systems and methods described herein may assist in real-time monitoring of time calibration for an array of positron emission detectors during a patient image scan and/or radiation therapy treatment. A PET detector that was improperly calibrated or which the calibration has changed during use and/or otherwise faulty (e.g., due to afterglow effects, malfunctions, etc.) may generate incorrect positron emission location data, which may in turn affect the quality of radiation therapy treatment and/or patient imaging. A change in a machine parameter or a calibration error may quickly be identified simultaneously during a radiation therapy treatment and/or imaging session. Because patient workflow does not need to be suspended during any quality assurance or calibration, this may increase patient throughput, and may reduce incorrect radiation dose to a patient. A radiation therapy system as described herein may include an array of positron emission detectors (e.g., PET detectors) and a calibration source holder for holding a calibration source (e.g., radiation source) at a predetermined (e.g., reference) location. The predetermined, expected location may be compared to an actual computed location of the calibration source calculated by the system using the positron emission detectors. If the locations do not fall within a specified range or within a threshold parameter, then one or more of the detectors may be out of calibration and/or faulty, and the system may respond by, for example, deactivating the detectors and/or halting an imaging and/or radiation therapy treatment based on positron emission data. The systems and methods may thus provide a safety mechanism to prevent incorrect radiation dose to a patient. In some variations, the imaging systems and methods described may further comprise a PET detector calibration monitoring system configured to monitor other parameters such as a temperature of the PET detector. Generation of a PET detector calibration fault signal may be corroborated with the temperature of the PET detector detected by the PET detector calibration monitoring system. In some variations, a discrepancy between the fault signal and the detected PET detector temperature may indicate a fault in the PET detector calibration monitoring system.

In some variations, the imaging systems and methods may be used with radiation therapy systems useful for high-energy photon delivery. A radiation treatment assembly may be useful for emission-guided radiation therapy, where gamma rays from markers or tracers that are localized to patient tumor regions may be detected and used to direct radiation to the tumor. Generally, the radiation therapy systems described herein may comprise a movable gantry, such as a rotating gantry, with positron emission detectors and a radiation treatment source (e.g., MV X-ray source) mounted on the gantry. The positron emission detectors may be mounted on the rotating gantry, and may acquire positron emission data (e.g., emissions from a PET tracer that preferentially accumulates in tumor tissue), and the radiation treatment source may deliver a radiation dose to the patient guided by the detector data and a treatment plan. In response to a determination that the positron emission detectors are out of calibration, delivery of further radiation dose may be prevented, thus increasing safety and reducing potential harm to the patient.

The calibration source (e.g., radiation source) for PET detector time calibration and/or fault detection may be compact and generate radioactivity sufficient for real-time calibration while minimizing additional radiation exposure to the patient and/or operator. For example, the radiation source may be located between the positron emission detectors (e.g., located in a gantry housing and/or in a bore of the gantry), spatially separated from the patient, and emit enough positrons giving rise to coincident photon events to be distinguishable over noise (e.g., cosmic rays). In some variations, the calibration source may be located within or on the surface of a (stationary) housing of the rotatable gantry on a top portion and/or a bottom portion of the bore. For example, the calibration source may be located on the surface of a housing of the rotatable gantry and co-planar with the positron emission detectors; that is, the positron emission detectors may define an imaging plane along a cross-sectional slice of the bore and the calibration source may be located on the housing such that it is co-planar with that slice (e.g., at any circumferential location of the bore, such as at the top or 0°, or the bottom or 180°, left side or 270°, right side or 90°, etc.). Furthermore, a calibration source holder may retain the radiation source at a location such that at least some of the photons originating from a positron annihilation event may travel along linear emission paths (e.g., LORs) that do not intersect with the patient scan or treatment region. Accordingly, calculated locations of the calibration source and patient derived from calibration source emission data and patient emission data may be spatially separated. For example, the location of the calibration source holder (and the radiation source retained within the holder) is not co-localized with the patient scan or treatment area.

The precision and/or functionality of the positron emission detectors may be monitored by comparing a calculated location of the calibration source with a reference location or location range of the calibration source. For example, calibration data including coincident photon emission time offsets may be compared to reference time offsets to compute a difference between the calculated location and reference location or location range of the calibration source. A difference exceeding a threshold parameter may generate a fault signal of the PET detectors. In some variations, fault detection may be performed using a stationary calibration source while the positron emission detectors are rotating. In other variations, the calibration source may comprise an annulus shape. In yet other variations, the positron emission detectors and calibration source may be fixed relative to each other and rotate about a bore of a gantry. For example, the PET detectors and calibration source may be mounted to a rotatable gantry.

I. Systems

Radiation Treatment Assembly

Disclosed herein are systems for delivering high-energy photons to a region of interest (ROI) of a patient while monitoring PET detector function and/or time calibration. FIG. 1A illustrates a block diagram of a radiation treatment assembly (100) for high-energy photon delivery and real-time PET detector fault detection. The assembly (100) may include a gantry (110) including positron emission (PET) detectors (112), an imaging radiation source (114), imaging detector (116), a treatment radiation source (118), a multi-leaf collimator (120), and a treatment radiation detector (122). The gantry (110) may be a movable gantry such as a rotatable gantry that rotates about a longitudinal axis of the gantry (110). For example, a treatment radiation source (118) may be disposed on a continuously rotatable gantry to generate a radiation beam at one or more gantry angles. In some variations, the gantry (110) may comprise a ring gantry, and/or may be rotatable about a bore and have an axis of rotation that is parallel to a longitudinal axis of a bore. In other variations, the gantry (110) may comprise a C-arm shape. The PET detectors (112) may comprise any number and configuration to detect positron emission data (e.g., a pair of 511 keV photons emitted by a positron annihilation event) generated within a patient scan or treatment region (e.g., within a bore) of the gantry (110). For example, an opposing pair of PET detectors may detect a pair of high-energy 511 keV photons and the timing difference between the photon pair may be used to calculate the location of a photon emission origin (i.e., location of a positron annihilation event) based on time of flight (TOF) of the photons. The positron emission detectors (112) may comprise, for example, a scintillation detector, comprising one or more of lutetium orthosilicate (LSO), lutetium-yttrium orthosilicate (LYSO), and lanthanum bromide (LaBr$_3$). The detectors may be disposed along at least a portion of a circumference of the gantry (110) and located generally opposite each other. The positron emission detectors (112) may be located at the same location along the length of the bore as the treatment radiation source (118) and multi-leaf collimator (120) (e.g., along the same tomographic slice). For example, the positron emission detectors may define an imaging plane along a cross-sectional slice of the bore and the treatment radiation source may be located on the gantry such that its irradiation plane or field is co-planar with that slice; that is, the treatment radiation source and the PET detectors may be co-planar (e.g., both mounted on the rotatable ring, arranged such that a beam plane of the treatment radiation source is co-planar with a detection plane of the PET detectors) or may both be located at the same longitudinal location along the bore (such that the radiation beam plane generated by the imaging radiation source may be co-planar with the radiation beam plane generated by the therapeutic radiation source).

A rotating mechanism (124) may be coupled to the gantry (110) and configured to rotate the gantry (110) from about 10 revolutions per minute (RPM) to about 70 RPM. In some variations, the rotating mechanism (124) may rotate the gantry (110) such that the detectors (112), imaging radiation source (114), imaging detector (116), treatment radiation source (118), multi-leaf collimator (120), and treatment radiation detector (122) may rotate about a rotational axis of the gantry (110). In some variations, the detectors (112) may rotate about the gantry (110) while in other variations the detectors (112) may be stationary.

The imaging radiation source (114) and a corresponding imaging detector (116) may be used to generate patient image data (e.g., CT images, MR images), and in some variations may comprise a kV source and kV detector. The patient image data may be used to register the patient (e.g., identify the patient's location with respect to the radiation treatment assembly components) and/or aid delivery of treatment radiation delivery to the patient. The treatment radiation source (118) may deliver a treatment radiation dose to the patient in a bore of the gantry and may comprise, for example, a linear accelerator (linac) and a magnetron (e.g., MV X-ray source). The treatment radiation beam may be shaped by a beam-shaping assembly coupled to the treatment radiation source (118) to deliver a prescribed radiation dose to the ROI using a plurality of radiation beams output from a plurality of gantry angles. For example, the beam assembly may comprise a multi-leaf collimator (120) coupled to the treatment radiation source (118) and may be located in a treatment radiation beam path for shaping the treatment radiation beam delivered to the patient. The multi-leaf collimator (120) may comprise a plurality of leaves and corresponding actuation mechanisms configured to independently move (e.g., open and close) the leaves in one or more axes (e.g., X-axis, Y-axis). For example, the multi-leaf collimator (120) may be a binary multi-leaf collimator. The treatment radiation detector (122) (e.g., MV detector) may oppose the treatment radiation source (118). The treatment radiation detector may be located along the treatment radiation beam path and may acquire treatment radiation data. The positron emission detectors (112) may be arranged such that they are not in the treatment radiation beam path. The treatment radiation source (118) may generate any type of ionizing radiation, for example, photon radiation (e.g., X-rays and gamma rays) and/or particle radiation (e.g., electrons, protons, neutrons, carbon ions, alpha particles, and beta particles). In some variations, the imaging radiation source (114) and treatment radiation source (118) may have separate components (e.g., linac, beam converter assembly) while in other variations the sources (114, 118) may share one or more components (e.g., share the same beam converter assembly).

Figure 1B:
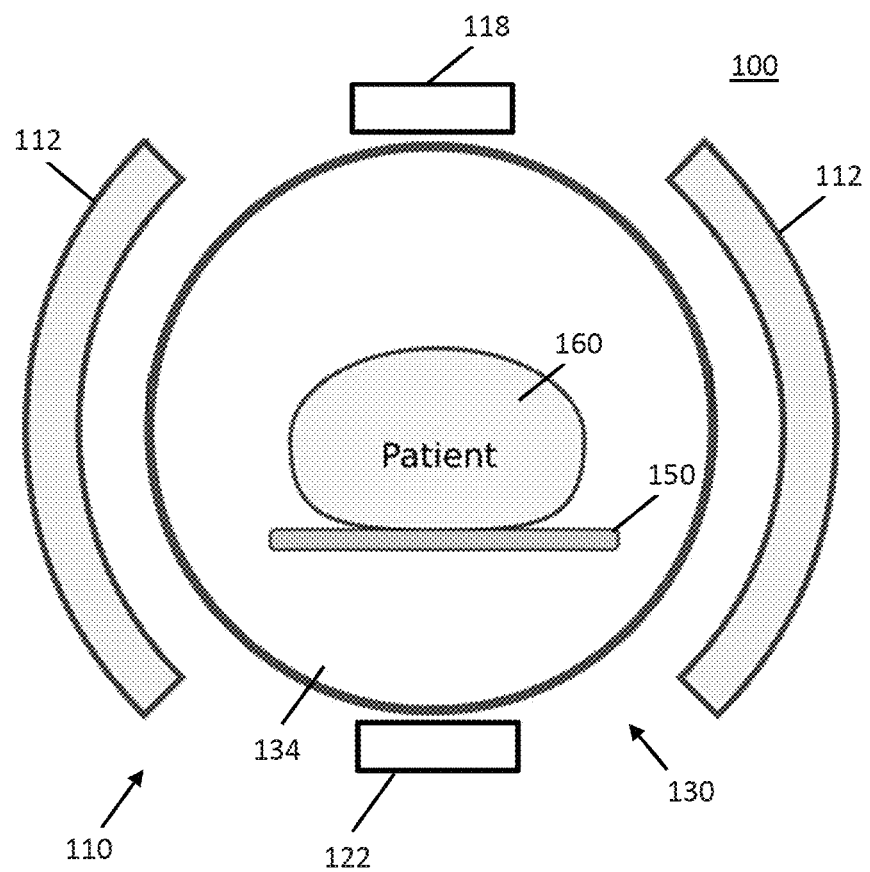
FIG. 1B is a schematic cross-sectional view of the radiation therapy assembly depicted in FIG. 1A.

The assembly (100) may further include a housing (130) configured to hold a calibration source (132), a processor (140), memory (142), and a patient support (150). FIG. 1B is a non-limiting schematic example of the radiation treatment assembly (100) depicted in FIG. 1A where calibration source (132) is not illustrated in FIG. 1B. The housing (130) may enclose the gantry (110) and provide a barrier between the patient (160) and the gantry (110). For example, the housing (130) may be coupled to the gantry (110) and provided between the patient support (150) (e.g., couch) and the positron emission detectors (112). The gantry (110) may rotate while the housing (130) remains stationary. The housing (130) may comprise a bore (134) or opening in which the patient (160) and patient support (150) may be disposed. For example, a patient (160) disposed on the patient support (150) may be moved in and out of the bore (134) of the housing (130).

The calibration source (132) may be a radiation source configured to generate radiation sufficient for the detectors (112) to locate the calibration source in real-time (e.g., during a patient image scan and/or patient treatment session) without exposing the patient and/or operator to significant additional radiation. In some variations, the calibration source may comprise a positron emitting material comprising one or more isotopes such as 22-Na, 68-Ge, 68-Ga, and the like. Emitted positrons may collide with electrons in an annihilation event to generate gamma rays (e.g., a pair of diametrically opposed photons) that travel along a linear path (e.g., line of response or LOR). Detected photon pairs are classified as a coincidence event if they are detected by opposing positron emission detectors (112) within a predetermined time window (e.g., coincidence time window). The detectors record the detection location and reception time. A reception time difference between a pair of coincidence photons is referred to as time of flight (TOF) and may be used to determine the origin of the positron annihilation event along the LOR. The TOF measurement exhibits uncertainty and corresponds to a timing resolution of the detectors (112). This uncertainty in the positron annihilation event and timing resolution may be represented or characterized by a probability distribution (e.g., Gaussian distribution) or related parameter, which may be further characterized by a Full Width at Half Maximum (FWHM) of the Gaussian distribution of the location derived from TOF measurement.

In some variations, the calibration source (132) may comprise a radioactivity of about 1 µCi to 300 µCi, e.g., about 2 µCi, about 100 µCi. Accordingly, the calibration source (132) may emit enough positrons per second (e.g., annihilation events) for the positron emission detectors (112) to receive positron emission data allowing the processor (140) to monitor PET detector calibration (e.g., distinguish positron emissions of the calibration source (132) from the emissions of the patient (160) using time offset data). The rate of positron-emission of the calibration source may be known and the emission rate (and optionally, the positron annihilation rate) may be used by the controller processor to determine whether the positron emission detectors are faulty and/or calibrated properly. For example, the LOR detection rate as measured by the positron emission detectors may be compared with the known positron-emission rate of the calibration source. If the LOR detection rate (i.e., the LORs and/or coincident photon events that may be attributed to the calibration source because the LORs intersect the known location of the calibration source and/or calibration source holder) is greater than or less than the known positron-emission rate (and/or an expected LOR emission rate calculated based on the known positron-emission rate) by specified tolerance thresholds, the processor may generate a notification to the user indicating that the LOR detection rate differs from the expected rate. Optionally, the controller processor may generate an interlock signal that pauses or ceases treatment radiation delivery until the user can verify that the positron emission detectors are functioning properly and/or calibrated.

A shape of the calibration source (132) is not particularly limited and may comprise any geometric shape such as a cylinder, sphere, ring, rod, disc, line source, etc. In one variation, a calibration source may comprise a housing or enclosure and a radioactive (e.g., positron-emitting) element located within the enclosure. The housing or enclosure may be disk-shaped and/or made of a non-radioactive or inert material, such as Mylar, Teflon, epoxy, and/or glass. The radioactive element may be embedded within the housing or enclosure. In some variations, the radioactive element may be a pellet, bead, seed, capsule, droplet, gel, etc., The calibration source (132) may be oriented in any direction so long as the calibration source (132) is located at the same location along the length of the gantry (110) as the PET detectors (112), i.e., co-planar with the PET detectors. For example, a rod shaped or line source shaped calibration source may be arranged in parallel with a longitudinal axis of the gantry (110). In some variations, the calibration source may (132) comprise a shape with a maximum dimension from about 0.25 inch to about 3 inches, e.g., about 1 inch, about 2 inches. In some variations, the calibration source (132) may comprise one or more positron-emitting capsules that each contain a quantity of positron-emitting tracer(s), where each capsule has a maximum dimension of about 2 cm. Some capsules may have a maximum dimension of no more than about 300 For example, a calibration source may comprise a disk-shape enclosure with a diameter of about one inch, a thickness of about 0.25 inch, and a radioactive capsule with a diameter of about 0.039 inch (e.g., about 1 mm). The radioactive capsule may be embedded within an epoxy well in the enclosure, about halfway through the thickness of the disk and at the center of the disk. Positron-emitting capsules or calibration sources that are relatively small (e.g., less than about 2 cm, less than about 1000 less than about 500 less than about 300 etc.) may be more easily contained or isolated (to prevent unwanted contamination) and may have a relatively longer half-life (e.g., about 2 years or more, about 2.6 years). The calibration source may comprise an array of positron-emitting capsules, arranged in a linear configuration and/or distributed radially about the bore (134). For example, a calibration source may be located at the top of a bore (e.g., at 0°), bottom of a bore (e.g., at 180°), or any radial or angular position about the bore (e.g., at 90°, 270°, 30°, 120°, 60°, 150°, 200°, 300°, etc.). In some variations, a plurality of calibration source may be located at radially and/or bilaterally symmetric locations about the bore (e.g., four sources at 0°, 90°, 180°, and 270°; two sources at 0° and 180°; four source at 30°, 150°, 210°, 330°, etc.). A calibration source (132) may comprise a first positron-emitting capsule at a first location about a bore or patient area, and a second positron-emitting capsule at a second location across from (e.g., about 180 degrees from) the first positron-emitting capsule. Alternatively or additionally, a first positron-emitting capsule may be located at a first end of a first array of PET detectors, a second positron-emitting capsule located at a second end of the first array of PET detectors, a third positron-emitting capsule located at a first end of a second array of PET detectors, and a fourth positron-emitting capsule located at a second end of the second array of PET detectors. More generally, the positron-emitting capsules of a calibration source may be located outside of a patient area or the bore of a gantry. The calibration source (132) or positron-emitting capsule may comprise a radioactive portion and a non-radioactive housing enclosing the radioactive portion. In one variation, the non-radioactive housing may be disc shaped and a radioactive portion may be spherical and located at a center of the disc. In another variation, a ring shaped radiation portion may be disposed in a disc shaped non-radioactive housing. In yet another variation, the non-radioactive housing may be cylindrical and a radioactive portion may be disposed in spaced apart wells located, for example, at the ends of the cylinder.

In some variations, the patient support (150) (e.g., couch) may comprise a support surface and a base (not shown) for control of positioning of a patient in the assembly (100). The base may be fixed to the ground and the support surface may be coupled to the base such that the support surface may move in and out of a bore of the gantry (110). The patient may be disposed on the support surface to be imaged and/or treated by the assembly (100) (e.g., the patient lying flat on the patient support (150)).

The processor (140) may incorporate data received from the memory (142) and positron emission detectors (112) to compute a location of the calibration source (132) based on detected emission data. Based on the calculated location, positron emission data may be classified as originating from one of the calibration source and the patient scan region. The memory (142) may further store instructions to cause the processor (140) to execute modules, processes and/or functions associated with the system (100), such as fault detection and safety (e.g., deactivation of one or more system components, stopping radiation therapy treatment, outputting system status, etc.). For example, the memory (142) may be configured to store location data of the calibration source (132), one or more threshold parameters, a patient treatment plan, one or more spatial filters, positron emission data (e.g., positron emission path data), calibration data, patient data, and operator input.

Memory (142) may store a location of the radioactive source held in the radioactive source holder. The processor (140) may be any suitable processing device configured to run and/or execute a set of instructions or code. The processor may be, for example, a general purpose processor, a Field Programmable Gate Array (FPGA), an Application Specific Integrated Circuit (ASIC), a Digital Signal Processor (DSP), and/or the like. The processor may be configured to run and/or execute application processes and/or other modules, processes and/or functions associated with the system and/or a network associated therewith (not shown). The underlying device technologies may be provided in a variety of component types, e.g., metal-oxide semiconductor field-effect transistor (MOSFET) technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, and/or the like.

The memory (142) may include a database (not shown) and may be, for example, a random access memory (RAM), dynamic random access memory (DRAM), static random access memory (SRAM), a memory buffer, a hard disk drive, optical disc, magnetic tape, an erasable programmable read-only memory (EPROM), an electrically erasable read-only memory (EEPROM), a read-only memory (ROM), Flash memory, solid state drive (SSD), memory card, etc. The memory (142) may store instructions to cause the processor (140) to execute modules, processes and/or functions associated with the system (100), such as fault detection.

The system (100) may be in communication with other devices (not shown) via, for example, one or more networks, each of which may be any type of network. A wireless network may refer to any type of digital network that is not connected by cables of any kind. Examples of wireless communication in a wireless network include, but are not limited to cellular, radio, and microwave communication. However, a wireless network may connect to a wireline network in order to interface with the Internet, other carrier voice and data networks, business networks, and personal networks. A wireline network is typically carried over copper twisted pair, coaxial cable or fiber optic cables. There are many different types of wireline networks including, wide area networks (WAN), metropolitan area networks (MAN), local area networks (LAN), Internet area networks (IAN), campus area networks (CAN), global area networks (GAN), like the Internet, and virtual private networks (VPN). Hereinafter, network refers to any combination of combined wireless, wireline, public and private data networks that are typically interconnected through the Internet, to provide a unified networking and information access solution. The system may be configured to provide not only patient diagnostic or therapeutic data, but also machine calibration data (e.g., calibration data) and QC data to the patient's electronic healthcare record and/or to electronic record systems used by accreditation agencies, such as the American College of Radiology, the Joint Commission, the UK Accreditation Services (UKAS), and the European Association of Nuclear Medicine's EARL program, for example.

Calibration Source

As described in detail below, a calibration source of a radiation therapy assembly may comprise a number of configurations and/or locations relative to the assembly. As used herein, a calibration source may be a radiation source comprising a substance that emits positrons within a field of view of the PET detectors sufficient to monitor a detector time calibration while minimizing dose to the patient. For example, the radioactive source described with respect to FIGS. 2-4 may emit photons with an energy of 511 keV for each positron annihilation event. In other variations, the radioactive source of a calibration source may comprise a substance that emits radiation having a different energy level. The calibration sources may be located on a radiation treatment assembly such that at least some lines of response originating from the calibration source do not intersect a patient and/or patient support disposed in a bore of the gantry. That is to say, the calibration source may intersect at least one line provided between opposing positron emission detectors and which are unobstructed by a patient and/or patient support (although the line may pass through other structures such as the gantry housing). As an illustrative example, the calibration source may be disposed along a housing coupled to the gantry at a location at least about 20 cm above the patient support. Spatial separation between the calibration source and the patient may reduce errors in a calculated location of the calibration source and the patient. A fault signal for one or more positron emission detectors may be generated using the positron emission data of the calibration source. The system may respond appropriately to the fault signal (e.g., output a detector status, deactivate faulty detectors, and/or stop treatment).

Figure 6A:
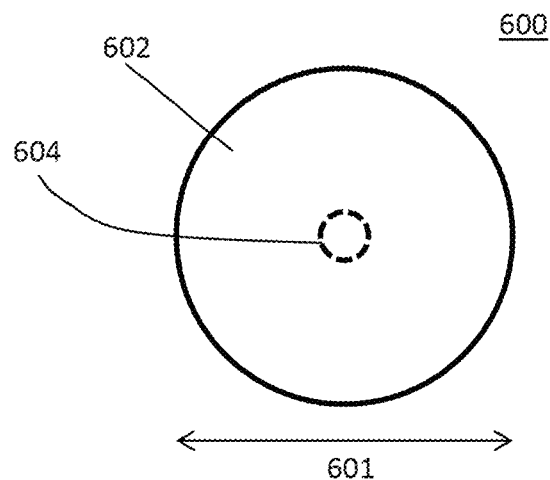
FIGS. 6A-6B are front and partial cross-sectional side views, respectively, of one variation of a calibration source.
Figure 6B:
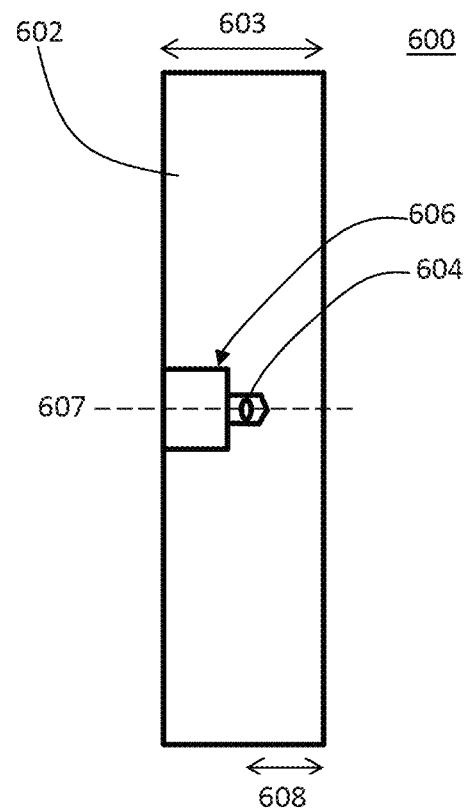

One variation of a calibration radiation source is depicted in FIGS. 6A-6B. As depicted there, calibration radiation source (600) may comprise a disk-shaped enclosure or housing (602) and a positron-emitting element (604) located within the enclosure, at the center of the disk. The enclosure (602) may be made of a non-radioactive material and may have a well (606) within which the positron-emitting element (604) may be located. In some variations, the enclosure (602) may be made as a solid disk, a well (606) may be created within the disk (e.g., optionally, located on the center of the disk as represented by the dotted line (607)), the positron-emitting element (604) may be inserted into the well (606), and the well may then be filled with a non-radioactive material, such as an epoxy. The diameter (601) of the enclosure (602) may be from about 0.25 inch to about 3 inch, e.g., about 1 inch, about 2 inches. The thickness (603) may be from about 0.1 inch to about 0.5 inch, e.g., about 0.25 inch. The size of the positron-emitting element (e.g., capsule) may be from about 150 µm to about 500 µm, e.g., about 200 µm, about 250 µm, about 300 µm, etc. The positron-emitting element (604) may be inserted or embedded such that it is halfway between the thickness of the disk. For example, the positron-emitting element (604) may be located at a distance (608) from one side surface of the enclosure (602), where the distance (608) may be from about 0.01 inch to about 0.4 inch, e.g., about 0.12 inch, about 0.2 inch, etc.

It should be understood that the systems described below do not require each of the components depicted above in FIG. 1. For example, a treatment radiation source (e.g., MV X-ray source) may not be included in the system variations depicted in FIGS. 2-4. The systems depicted in FIGS. 2-4 may be imaging systems that do not have a treatment radiation source, or they may be radiation treatment systems with a treatment radiation source that has been omitted for ease of explanation.

A. Stationary Calibration Source

Figure 2A:
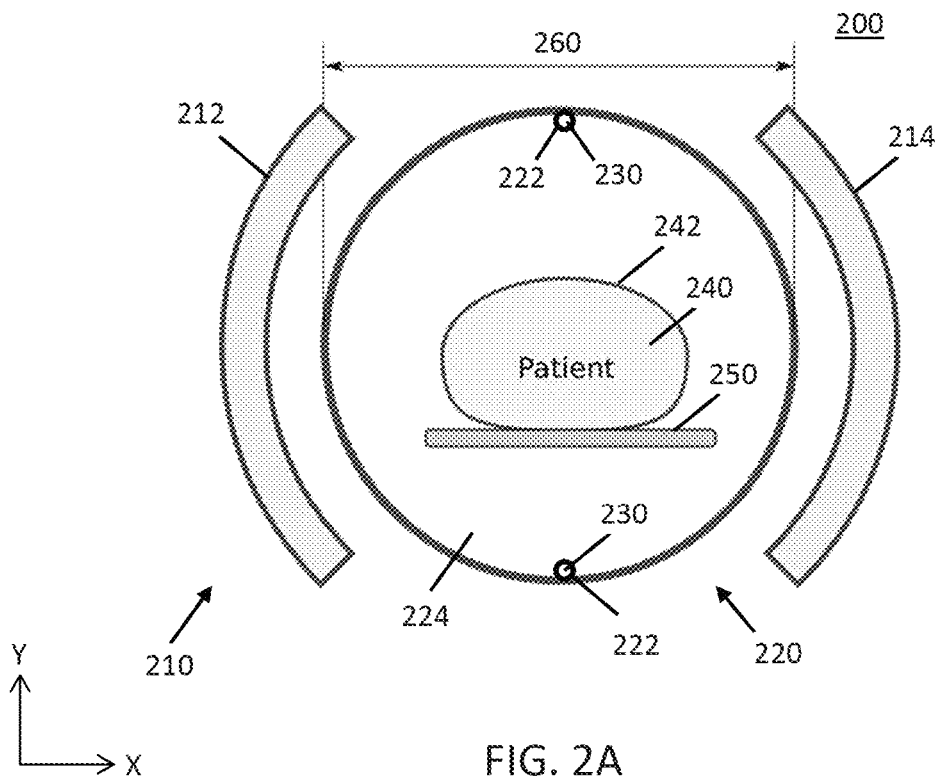
FIGS. 2A-2B are illustrative cross-sectional views of a variation of a radiation therapy assembly.
Figure 2B:
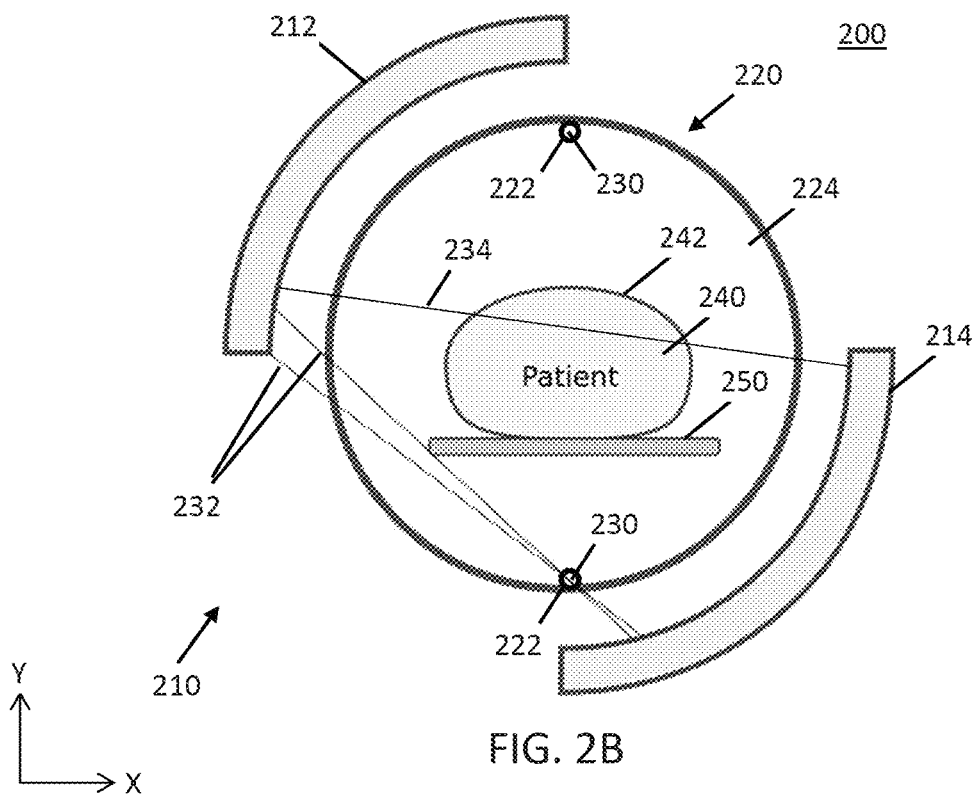

Variations of an imaging assembly described here may comprise a plurality of positron emission detectors and a stationary calibration source for real-time PET detector fault detection. FIGS. 2A-2B are cross-sectional schematic views of a radiation treatment assembly (200) including a rotatable gantry (210) having mounted thereon a first array of positron emission detectors (212) and a second array of positron emission detectors (214) opposing the first array of detectors (212). Each array of detectors (212, 214) may comprise a plurality of positron emission detectors. A housing (220) may couple to the gantry (210) (e.g., the housing (220) may be disposed over the gantry (210)), and the housing (220) may comprise a bore (224) in which a patient support (250) may be disposed. Each positron emission detector has an imaging field of view that is the angle through which that detector is sensitive to positron emissions. As used herein, a patient scan region (242) (e.g., patient imaging field of view) may be represented by a volume of a patient (240) and/or patient support (250). That is, the contours of the patient (240) and/or the patient support (250) detectable by the positron emission detectors may define a patient scan region (242). The patient support (250) may comprise a movable support surface on which the patient (240) may be disposed. The movable support surface may be coupled to a base (not shown).

The housing (220) may comprise a stationary calibration source holder (222) and/or calibration source (230) (e.g., radiation source) spaced away from the patient scan region (242) within the bore (224) and within a field of view of the positron emission detectors (212, 214). For example, the calibration source holder (222) and/or calibration source (230) may be located on a surface of the housing (220) (e.g., facing the patient support (250)). For the sake of illustration, the calibration source holders (222) and/or calibration sources (230) of FIGS. 2A-2B project from the housing (220) towards the patient (240) although other variations are contemplated. For example, the calibration source holder (222) and/or calibration source (230) may be located within a recess or within the housing (220) between the first array and second array of detectors (212, 214). The assembly (200) may comprise a single calibration source holder (222) and calibration source (230) where FIGS. 2A-2B illustrate two calibration source holders (222) and calibration sources (230) for ease of explanation, however, it should be understood that in some variations, there may be a single calibration source holder and calibration source at either of the locations depicted in the figures (e.g., only at the top or only at the bottom portion of the bore), or additional calibration source holders and calibration sources at additional locations around the bore. The calibration source holder (222) may be configured to hold any of the calibration sources described herein (e.g., a positron emitting radiation source). The calibration source holder (222) may securely hold the calibration source (230) at a desired location (e.g., reference location or location range) using any known means, including but not limited to adhesives, a closure mechanism, and an interference fit or mechanical interfit between the calibration source holder (222) and calibration source (230). A closure mechanism may include a cap, cover, lid, plug, latch, lock, threaded ring, and combinations thereof. The calibration source holder (222) may allow the calibration source (230) to be removably coupled to the housing (220) such that the calibration source (230) may be replaced after its useful lifespan.

In some variations, the calibration source holder (222) may be disposed along the surface of the housing (220) at a location furthest from the patient scan region (242). In one example, the calibration source holder (222) may be disposed at a top, center location of the housing (220) (e.g., where the calibration source holder (222) is disposed). This location may be the furthest away from the patient (240) and therefore provide the least amount of additional dose from the calibration source (230) to the patient (240). In particular, a patient support (250) may be disposed below a rotational axis of the gantry (210) (e.g., mechanical isocenter axis) such that the patient (240) on the patient support (250) intersects a rotational axis of the gantry (210). Therefore, a distance from a top, center location of the housing (220) to the patient (240) may be greater than the distance of any other point along the surface of the housing (220).

In some variations, the calibration source holder (222) may be disposed along the surface of the housing (220) above or below the support surface of the patient support (250). The calibration source holder (222) may be disposed above a horizontal plane of the patient support (250) and/or perpendicular to the patient support (250). In some of these variations, the calibration source holder (222) may be disposed above the patient scan region (242). For example, the calibration source holder may be disposed at least about 20 cm above the support surface of the patient support (250). In other words, the calibration source holder (222) disposed along the surface of the housing (220) may be above the highest point of the patient (240). In other variations, the calibration source holder (222) may be disposed below a horizontal plane of the patient support (250) and/or perpendicular to the patient support (250). For example, as shown in FIGS. 2A-2B, the calibration source holder (222) may be disposed at a bottom, center location of the bore (224).

FIG. 2B illustrates the first array and second array of detectors (212, 214) at a second position rotated relative to the detectors (212, 214) at a first position in FIG. 2A. The positron emission detectors (212, 214) detect photon pairs emitted by the calibration source (230) and patient (240). The photon pair travels along a line of response (232) originating from the calibration source (230) and extending towards the first array of detectors (212) and the second array of detectors (214). At least some of the calibration source LORs (232) are non-intersecting with the patient scan region (242) (e.g., patient imaging field of view of the detectors including patient (240) and/or patient support (250)) such that at least some of the calibration source LORs (232) are spatially separated from patient lines of response (234) emitted from the patient (240). Consequently, the calibration source holder (222) is located for a calibration source (230) to form at least one LOR (232) unobstructed by the patient (240) and/or the patient support (250). Although not illustrated in FIGS. 2A-2B, the gantry (210) may further comprise a treatment radiation source and treatment detector between the first array and second array of detectors (212, 214) having a treatment field of view (260).

In some variations, a stationary calibration radiation source holder may comprise a groove or recess within an internal wall of the bore, or may be a groove or recess within a structure that may be attached to an internal wall of the bore. Optionally, a cover may be removably disposed over the groove or recess to retain the calibration source within the groove or recess, and engaged over the groove or recess via any attachment mechanism (e.g., snap-fit, friction-fit, screw-fit, with or without the use of additional one or more screws or fasteners). When the calibration source is to be replaced, the optional cover may be removed.

Figure 7A:
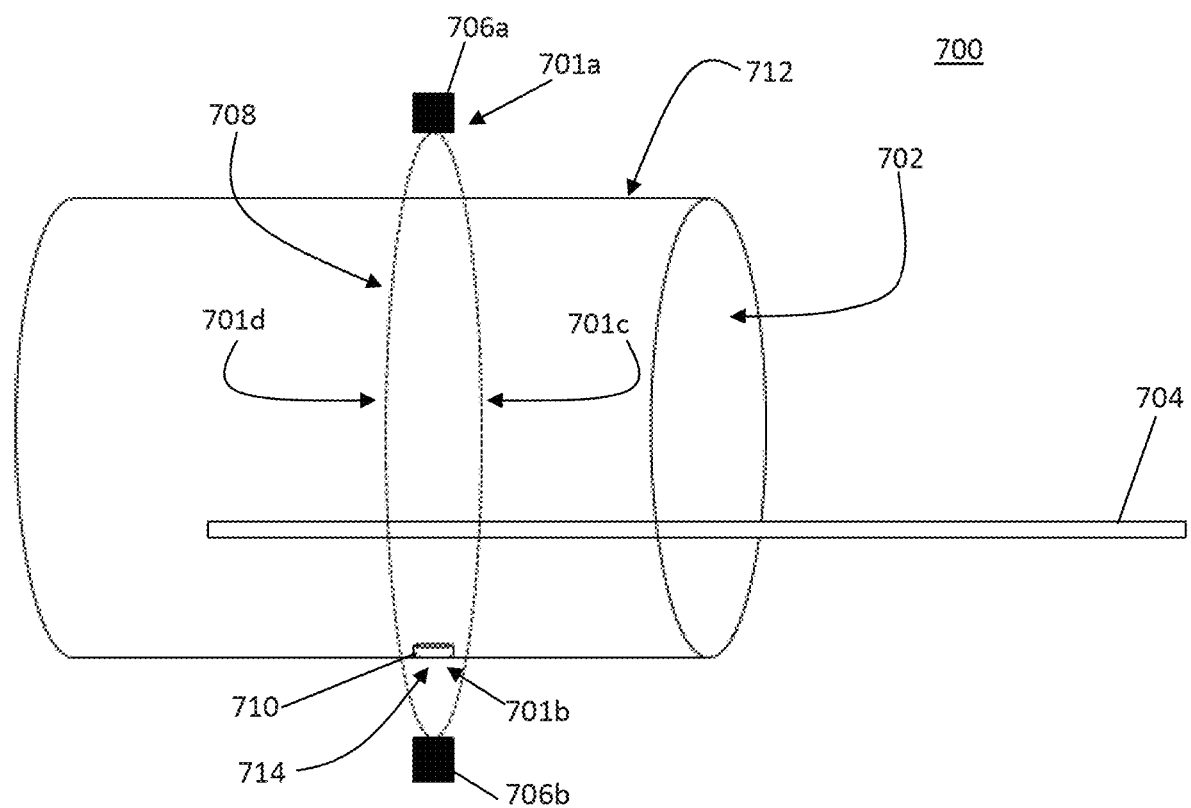
FIG. 7A is an illustrative schematic of one variation of a system comprising a calibration source.

FIG. 7A depicts one variation of a radiation treatment assembly or imaging system (700) comprising a bore (702) and a patient platform (704) movable along a longitudinal axis of the bore (702). The system (700) may comprise a rotatable gantry (not shown) that may have an axis of rotation that is collinear with the central axis of the bore (702), and a first array of positron emission detectors (706a) mounted on the gantry and a second array of positron emission detectors (706b) mounted on the gantry across from (i.e., opposite to) the first array of positron emission detectors (706a). The first and second array of positron emission detectors may be located along a plane or slice (708) of the bore (e.g., orthogonal to the longitudinal axis of the bore). In variations where the system (700) is a radiation treatment assembly comprising a treatment radiation source mounted on the rotatable gantry between the first and second positron emission detector arrays, the treatment beam plane may be co-planar with the positron emission detector slice (708). In this variation, a calibration radiation source (710) and the calibration radiation source holder (714) may be located within the bore (702), at a bottom location (701b) of the bore, below the patient support (704). Alternatively or additionally, calibration radiation sources and/or holders may be located at one or more circumferential locations about bore (e.g., at 701a or 0°, at 701b or 180°, at 701c or 90°, and/or at 701d or 270°, above the patient support, etc.). The calibration source holder (714) may be a groove or recess within an internal surface of the bore (702), with or without a cover, as described above. In some variations, a calibration source holder located above the bottom region of a bore may comprise a cover to prevent the calibration source from falling out, while a calibration source holder located at the bottom of the bore may not have a cover. Where a calibration source (710) has a disk-shape, the calibration source holder (714) may also have a corresponding disk-shape.

In some variations, the calibration radiation source holder may be integral with, and/or a part of, a housing of other components of the system. For example, any of the systems described herein may comprise one or more optical cameras and/or light sources within a bore, and comprise a camera and/or lighting mount attached to the internal wall of the bore. In some variations, the camera and/or lighting mount may comprise a groove or recess that is configured to be retain a calibration source (i.e., configured to be a calibration radiation source). For example, the camera and/or lighting mount may comprise a recess that has a size and shape that corresponds with the size and shape of a calibration source and an optional calibration source engagement structure, such as a cover (such as any of the covers described above), clasp, and/or magnetic source holder. Optionally, the calibration radiation source holder and/or mount may have one or more alignment structures, such as one or more grooves and/or protrusions that may help to retain the calibration radiation source in precise alignment with the other components of the radiation treatment assembly. For example, the holder and/or mount may have one or more protrusions that restrict motion of the calibration source in a first direction (e.g., IEC-Y) and/or one or more additional protrusions that restriction motion of the calibration source in a second direction (e.g., IEC-X). In some variations, one or more protrusions may include a wall portion of a camera and/or lighting mount. Alternatively or additionally, a groove or slot within which the calibration source may be seated may restrict motion of the calibration source. In some variations, the holder and/or mount may be centered or aligned with an isocenter of the system (e.g., along a central longitudinal axis of the bore).

Figure 7B:
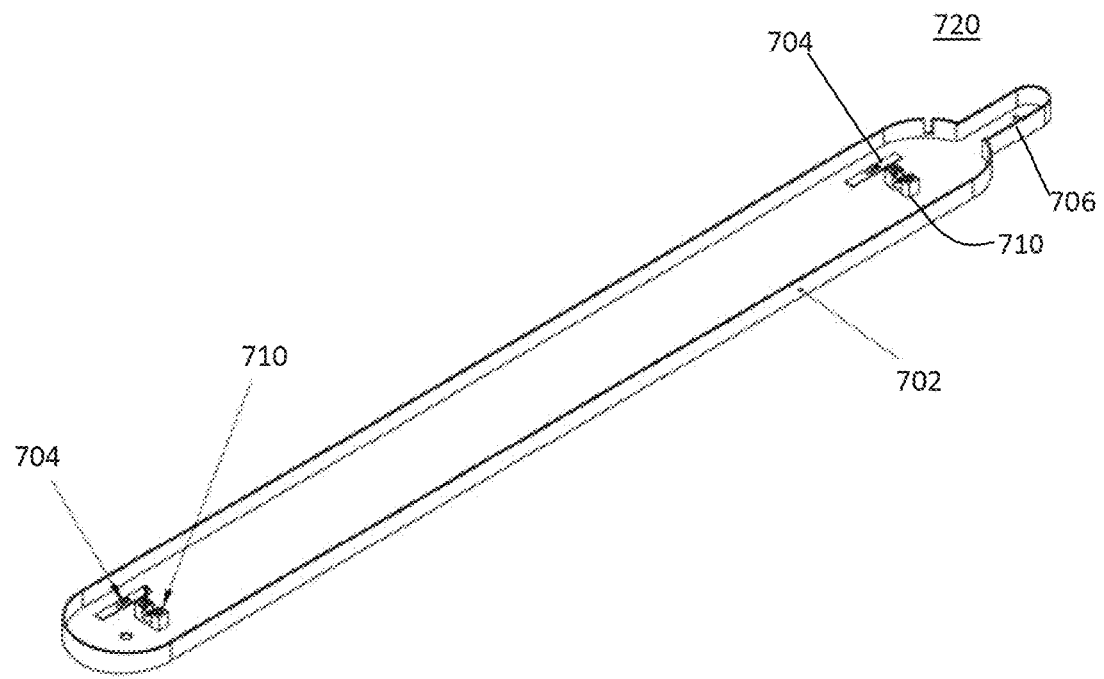
FIGS. 7B-7C are elevated perspective and top views, respectively, of one variation of mount that retains a calibration source.
Figure 7C:
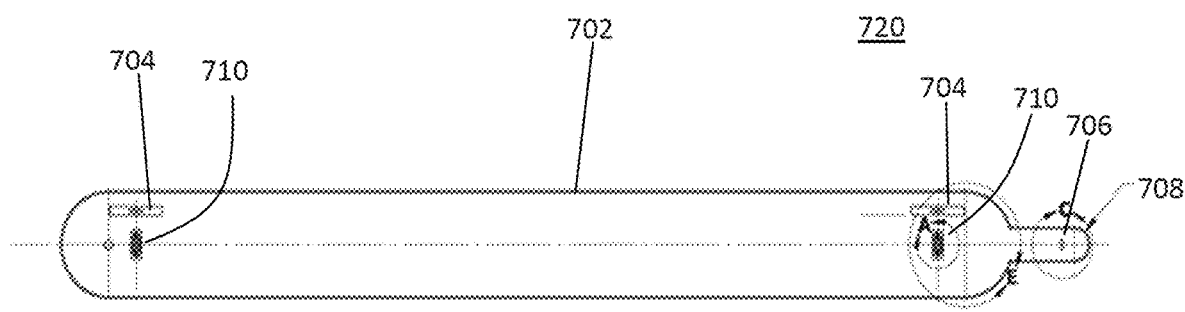

FIGS. 7B-7C depict an elevated perspective view and a top view, respectively, of a lighting mount that may be attached to an internal surface or wall of the bore, the lighting mount comprising a calibration source holder. One or more light sources, such as LEDs, may be attached to the internal surface of the bore via the lighting mount. A lighting cover having a corresponding shape and size (e.g., footprint) as the light mount may be disposed over the mount. Turning to FIGS. 7B and 7C, the lighting mount (700) may comprise a walled tray or enclosure (702) comprising one or more bore attachment structures (704), a calibration source holder alignment protrusion (706) and a calibration source receiving portion or holder (708). The calibration source holder or receiving portion (708) for a calibration source shaped as a circular disk may comprise a circular recess that has a diameter that is slightly larger than the diameter of the circular disk so that the calibration source may be retained within the recess. The bore attachment structure (704) may comprise a bracket that engages a corresponding notch on the internal wall of the bore, and/or may comprise structures for a screw-fit or any other such engagement with the bore. Optionally, the lighting mount (720) may also comprise one or more cover attachment structures (710), which may comprise a clip or clamp that may be used to retain or grasp a corresponding protrusion, flap, or tongue of an optional lighting cover (not shown). In the variation depicted in FIGS. 7B-7C, the lighting mount (720) may have an elongated oblong shape, where the calibration source holder or receiving portion (706) may be located at one end of the elongated shape. For example, the walled enclosure (702) may comprise a main oblong portion where the one or more light sources may be attached and a narrow extension to the main oblong portion where the calibration source holder or receiving portion may be located. This may help to segregate the calibration radiation source from the light sources, which may help reduce radiation damage to the light sources.

While the variations described herein may be directed to a system with a single calibration radiation source and/or a single calibration radiation source holder, it should be understood that similar structures and features may apply to systems with a plurality of calibration radiation sources and/or calibration radiation source holders. For example, a plurality of calibration radiation sources and/or holders may be distributed circumferentially about the bore, at a plurality of bore angles (e.g., bore angle locations 701a-701d, as well as angles between).

B. Annular Calibration Source

Figure 3:
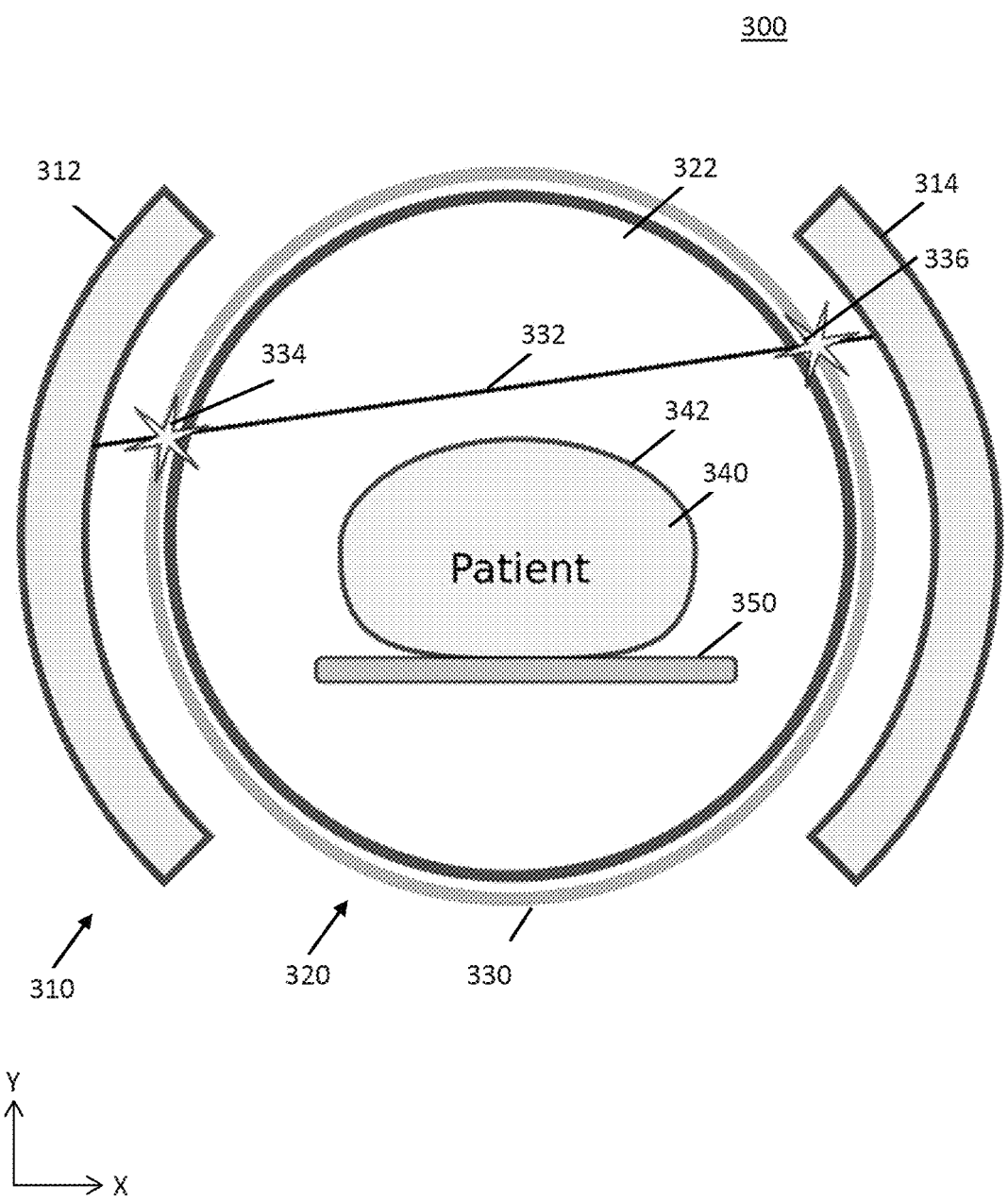
FIG. 3 is an illustrative cross-sectional view of another variation of a radiation therapy assembly.

FIG. 3 is a cross-sectional schematic view of a radiation treatment assembly (300) that may be configured to provide real-time calibration monitoring of PET detectors and include a gantry (310) having a first array of positron emission detectors (312) and a second array of positron emission detectors (314) opposing the first array of detectors (312). Each array of detectors (312, 314) may comprise a plurality of positron emission detectors and mounted to a movable or stationary gantry. Accordingly, the PET detector arrays may rotate or be stationary. A housing (320) may couple to the gantry (310) (e.g., the housing (320) may be disposed over the gantry (310)), and the housing (320) may comprise a bore (322) in which a patient (340) and a patient support (350) may be disposed. A patient scan region (342) (e.g., patient imaging field of view) may be represented by a volume of the patient (340) and/or patient support (350). That is, the contours of the patient (340) and/or the patient support (350) detectable by the positron emission detectors may define a patient scan region (342). The patient support (350) may comprise a movable support surface on which the patient (340) may be disposed and the movable support surface may be coupled to a base (not shown).

The housing (320) may further comprise an annular calibration source (330) (e.g., annular radiation source) about at least a portion of the bore (322). The radioactivity level of an annular calibration source may be similar to the radioactivity level of any of the calibration sources described herein, e.g., about 1 μCi to 300 μCi, e.g., about 2 μCi, about 100 μCi. For example, the annular calibration source (330) may be stationary and located below a surface of the housing (320) and/or may comprise the surface of the housing (320). The annular calibration source (330) may be located between the first array and second array of detectors (312, 314). As shown in FIG. 3, the annular calibration source (330) may comprise a continuous annulus. Regardless of the configuration of the positron emission detectors (312, 314) (e.g., rotatable or stationary), the annular calibration source (330) may be located within a field of view of the positron emission detectors (312, 314).

The positron emission detectors (312, 314) detect photons emitted by the annular calibration source (330) and patient (340). FIG. 3 illustrates an annular calibration source LOR (332) intersecting the annular calibration source (330) at a first location (334) and a second location (336). The LOR (332) may be unobstructed by the patient (340) and/or the patient support (350). The positron annihilation event corresponding to the LOR (332) may originate from either the first or second location (334, 334) of the annular calibration source (330). A TOF PET system may use a reception time difference (e.g., timing distributions) of the coincidence photons detected by the first array of detectors (312) and second array of detectors (314) to classify the first location (334) or second location (336) as the origin of the positron annihilation event. The timing distributions of the first and second locations of the annular calibration source (330) are different from timing distributions of positron emissions originating from a patient scan region (342) of the patient (340) because the annular calibration source (330) is located closer to the detectors (312, 314) than the patient (340), and therefore has a larger positron emission reception time difference than that of the emissions from the patient located closer to a center of the bore.

The first and second arrays of positron emission detectors may generate positron emission data from the annular calibration source (330) and the patient (340). A processor of the assembly (300) may distinguish the positron emission data from the patient (340) and from the annular calibration source (330). For example, the assembly (300) may concurrently classify (e.g., locate) the positron emission data from the annular calibration source (330) and the patient scan region (342) within the bore (322) using the reception times of the received photon pairs (e.g., using TOF data). A spatial filter may then be applied to the calculated locations, as discussed in more detail below.

In some variations, the annular calibration source (330) may comprise one or more portions (e.g., an upper portion disposed above a plane of the support surface (350) and a lower portion disposed below the plane of the support surface (350)). In some of these variations, an upper portion of the annular calibration source (330) may be disposed above the patient scan region (342). For example, the annular calibration source (330) may be disposed at least about 20 cm above the support surface of the patient support (350) and/or above the highest point of the patient scan region (342) (e.g., above a plane intersecting the highest point of the patient scan region (342) and parallel to the patient support (350)). In another variation, a lower portion of the annular calibration source (330) may be disposed below a horizontal plane of the patient support (350). These exemplary annular calibration source (330) configurations may provide less additional dose to a patient relative to an annular calibration source (330) that encircles the patient (340) entirely. The annular calibration source (330) may be attached to the housing (320), and the housing (320) may be removably attached to the gantry (310), thereby allowing the housing (320) and annular calibration source (330) to be replaced after its useful lifespan. The annular calibration source (330) may comprise a thickness of about 0.10 mm to about 2.0 mm and a width of about 0.10 mm to about 5 cm. In some variations, the annular calibration source (330) may comprise a plurality of portions with each portion having different shapes and dimensions.

C. Rotating Calibration Source

Figure 4:
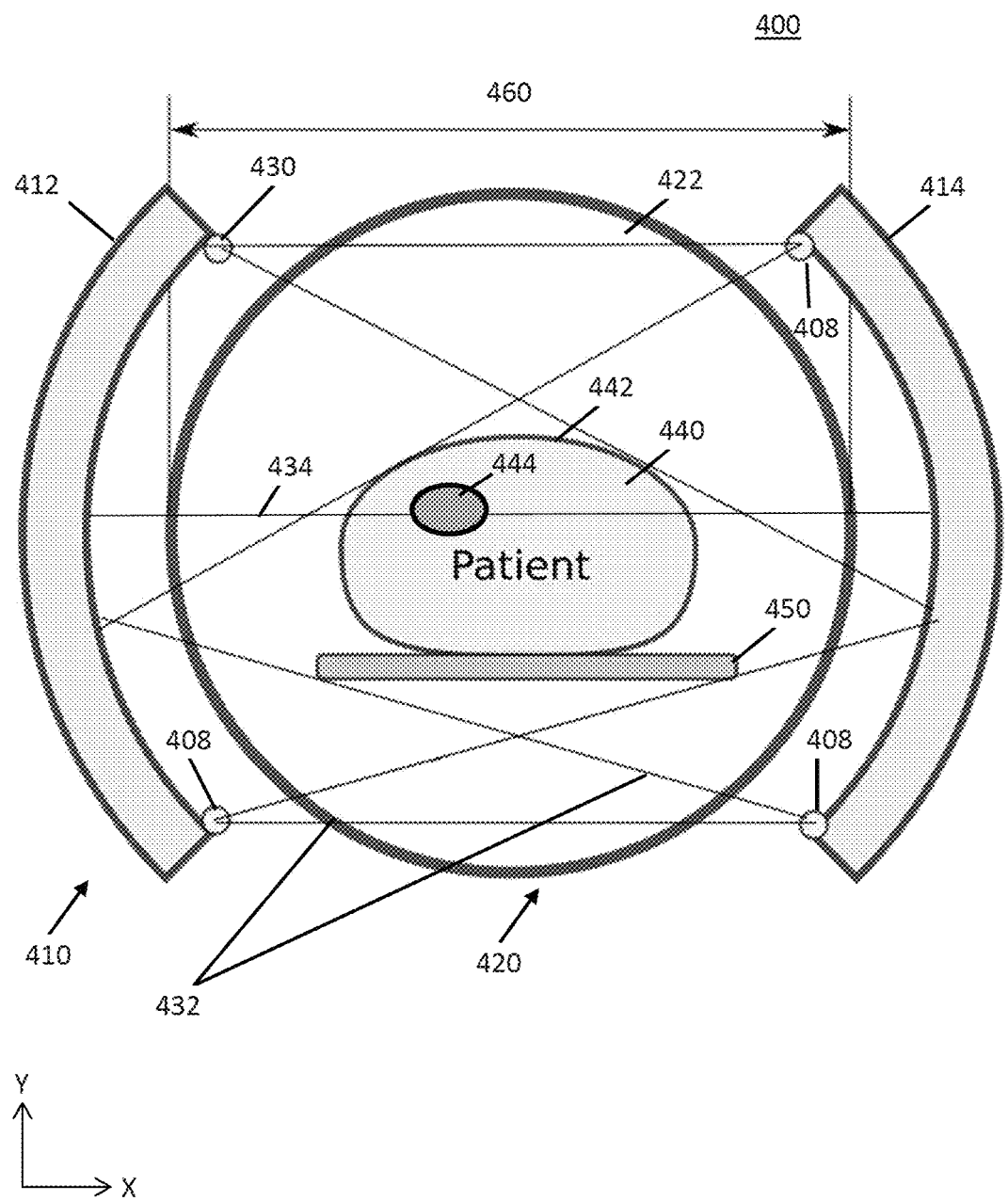
FIG. 4 is an illustrative cross-sectional view of yet another variation of a radiation therapy assembly.

FIG. 4 is a cross-sectional schematic view of an assembly (400) that may be configured to provide real-time calibration monitoring of PET detectors and include one or more calibration source holders (408). The radiation treatment assembly (400) may include a rotatable gantry (410) having mounted thereon a first array of positron emission detectors (412) and a second array of positron emission detectors (414) opposing the first array of detectors (412). Each array of detectors (412, 414) may comprise a plurality of positron emission detectors. In some variations, one or more calibration source holders (408) may be coupled to the gantry (410) such that the one or more calibration source holders (408) are fixed relative to the first array and the second array of detectors (412, 414). In other words, the positron emission detectors (412, 414) and calibration source holders (408) rotate together.

A housing (420) may couple to the gantry (410) (e.g., the housing (420) may be disposed over the gantry (210)), and the housing (220) may comprise a bore (422) in which a patient (440) and a patient support (450) may be disposed. A patient scan region (442) (e.g., patient imaging field of view) may be represented by a volume of the patient (440) and/or patient support (450) detectable by the detectors (412, 414). The patient support (450) may comprise a movable support surface on which the patient (440) may be disposed and the movable support surface may be coupled to a base (not shown).

As illustrated in FIG. 4, the one or more calibration source holders (408) and/or calibration sources (430) (e.g., radiation sources) may be spaced away from the patient scan region (442) within the bore (422) and within a field of view of the positron emission detectors (412, 414). For example, one or more calibration source holders (408) and/or calibration sources (430) may be coupled to the detectors (412, 414) and movable relative to the housing (420) (e.g., rotate about the housing (420)). For example, the one or more calibration source holders (408) and/or calibration sources (430) may be disposed along the detectors (412, 414) on a side facing an opposing detector (414, 412).

At least some of the lines of response (432) originating from one or more calibration sources (430) extend toward the first array of detectors (412) and the second array of detectors (414). As depicted in FIG. 4, at least some of the calibration source LORs (432) are non-intersecting with the patient scan region (442) and/or patient support (450). LORs (434) may be emitted from an ROI (444) of the patient (440). LORs (432) emitted by the calibration sources (430) may be detected by the positron emission detectors (412, 414). Consequently, each calibration source holder (408) is located for a calibration source (430) such that at least one LOR (432) emitted by the calibration source (430) is unobstructed by the patient (440) and/or the patient support (450). In some variations, one or more calibration source holders (408) may be located along a line non-intersecting with a patient imaging field of view (e.g., patient scan region (442)) of the detectors (412, 414), and the line may extend from the first array of detectors (412) to the second array of detectors (414). The patient imaging field of view may comprise a volume located between the first array and second array of detectors. In other words, one or more calibration source holders (430) may be fixed relative to the first array and the second array of detectors (412, 414) and located with at least one line of sight unobstructed by a patient (440) and/or patient support (450), although the line may pass through other structures such as the housing (420).

It should be noted that the assembly (400) may comprise a single calibration source holder (408) where the exemplary FIG. 4 illustrates four calibration source holders (408) and calibration sources (430). The calibration source holder (408) may be configured to hold the calibration source (430) in a manner as described in detail above. The calibration source holder (408) may allow the calibration source (430) to be removably coupled to the detectors (412, 414) such that the calibration source (430) may be replaced after its useful lifespan. Although not illustrated in FIG. 4, the gantry (410) may further comprise a treatment radiation source and treatment detector between the first array and second array of detectors (412, 414) having a treatment field of view (460).

II. Methods

Also described here are methods for generating a fault signal during delivery of treatment radiation and/or patient imaging using the systems and assemblies described herein. The system may comprise first and second arrays of PET detectors mounted on a rotatable gantry, where the PET detectors are configured to receive positron emissions from a calibration source (e.g., radiation source) and/or a patient to generate calibration data and/or to extract positron emission data representing positron emission activity originating from the calibration radiation source. That is, calibration data may comprise data extracted from the acquired positron emission data that pertains to the calibration source, and in some variations, may also include any data quantity calculated based upon acquired positron emission data, such as calculated location data of the calibration source and/or patient. In some variations, positron emissions from the calibration source may be distinguished from the positron emissions from a patient by identifying the LORs that do not cross or intersect with a patient scan or treatment region of the bore. Examples of calibration data may include spatial resolution data, temporal resolution data, energy sensitivity data and/or energy precision data, and/or the ability to accurately determine the location of the calibration radiation source. In some variations, calibration data may include the number of detected LORs that intersect with the location of a stationary calibration source over one or more gantry rotations, and/or the energy level(s) of the detected LORs (i.e., the coincident photon events) over one or more gantry rotations, and/or the number of detected LORs or coincident photon events detected within coincidence time windows having different window widths. If the calibration data exceeds a threshold parameter, such as when the calibration data does not sufficiently correspond to a reference location or location range of the calibration source for a predetermined time period, a fault signal may be generated.

Other examples of calibration data deviations that may trigger the generation of a fault signal may include detecting a greater (or lesser) number of LORs that intersect with the location of the stationary calibration source than is expected (based on the known and specified positron emission rate and/or radioactivity of the calibration source), detecting LORs having energy level(s) that deviate from a 511 keV peak, and/or not detecting a threshold number of LORs or coincident photon events with specific time difference values (e.g., time differences that correspond to one or more of PET detectors being close to the calibration source while other PET detectors are located far from the calibration source) and/or within a first coincidence time window centered around a time difference value of 0 ns (i.e., the number of "true" coincident photon events). Alternatively or additionally, if the number of coincident photon events detected within a second coincidence time window centered around a non-zero time different value (i.e., the number of "random" coincident photon events) exceeds the number of coincident photon events detected within the first coincidence time window (i.e., the number of "true" coincident photon events), a fault signal may be generated. The system may respond in one or more ways to the fault signal including performing additional diagnostics on the detectors and/or assemblies (e.g., gantry motion sensor and/or encoder diagnostics/characterization, calibration radiation source diagnostics/characterization, etc.), deactivating one or more detectors, stopping radiation therapy treatment, and/or recalibrating the detectors. It should be appreciated that any of the systems described herein may be used to determine a fault in the detectors using the methods discussed below.

Figure 5A:
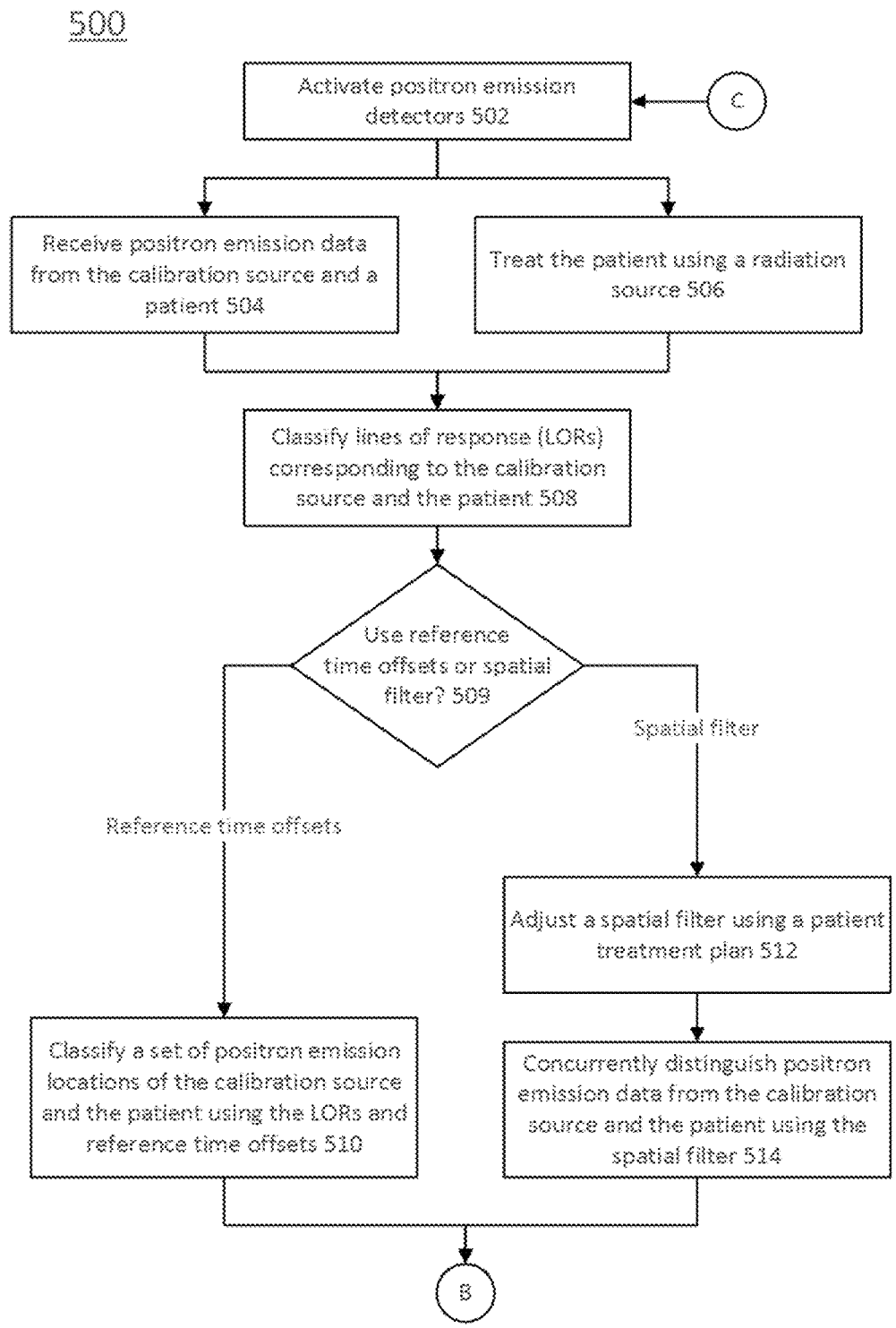
FIGS. 5A-5B are illustrative flowcharts of a variation of a method for fault detection.
Figure 5B:
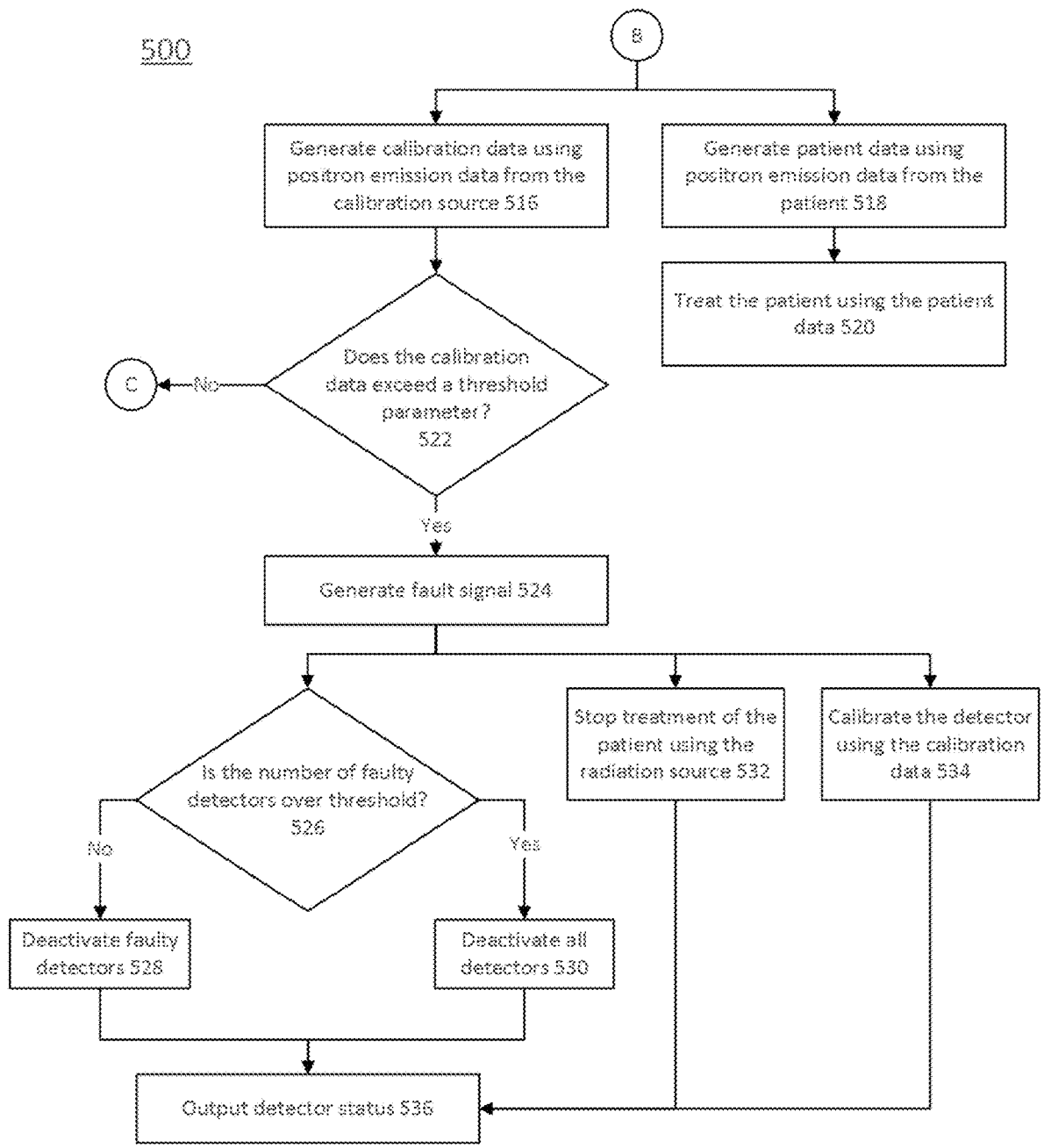

FIGS. 5A-5B illustrate a fault detection method (500) using any of the assemblies (100, 200, 300, 400) discussed above. For example, a radiation treatment assembly may comprise a gantry comprising a plurality of positron emission detectors, an imaging radiation source, a treatment radiation source, and one or more calibration sources provided between the detectors. For example, one or more calibration sources may be disposed in a housing within a field of view of the positron emission detectors and located at the same location along the length of the assembly as the positron emission detectors. The positron emission detectors and one or more calibration sources may be configured in various combinations of stationary and rotatable elements, as discussed in detail above. Prior to an imaging and/or radiation therapy procedure, a patient may be administered a radioisotope for uptake into the body. The patient may lay on a patient support (e.g., couch) and be moved into a bore of a gantry such that a ROI of the patient (e.g., one or more tumors or lesions) may be within a field of view of the positron emission detectors. Both the patient and the calibration source may be provided between the detectors with the calibration source spaced away from the patient. For example, the patient may be disposed within a bore of the assembly and the calibration source held by a calibration source holder on a surface of the housing.

An array of positron emission detectors may be activated to detect positron emissions emitted within a detector field of view (502). In some variations, the positron emission detectors may be mounted on a rotatable gantry where the gantry is configured to rotate about a bore of the gantry while in other variations the detectors may be mounted on a stationary gantry.

The positron emission detectors may receive positron emission data from any positron emission source provided between the detectors. For example, positron emission data from the patient and the calibration source may be continuously received and processed (504). The positron emission data may include TOF data such as a detector reception location and reception time of the photon by that detector. Concurrently, the patient may be treated by receiving a treatment radiation dose from the treatment radiation source (506). That is to say, positron emission data may be received during a treatment session. While positron emission data may be acquired during a treatment session, the timing of the positron emission data acquisition may be staggered with respect to the timing of the treatment beam pulses. For example, positron emission data may be received by the positron emission detectors at predetermined time intervals between treatment radiation beamlets. The patient may receive radiation therapy treatment from treatment modalities including, for example, emission-guided radiation therapy (EGRT), stereotactic body radiation therapy (SBRT), and intensity modulated radiation therapy (IMRT). Additionally or alternatively, the patient may be concurrently imaged by an imaging radiation source. The patient treatment and/or imaging step (506) may be performed in parallel (e.g., within a predetermined time period) with one or more of the steps of FIGS. 5A-5B. For example, the method (500) may perform one or more imaging and treatment steps (506) with the reception of the positron emission data (504) and/or generation of calibration data (516) with at least some temporal overlap. As another example, the step of receiving positron emission data from the calibration source and from the patient (504) may be performed concurrently with generating a fault signal (524).

An annihilation event comprising a photon pair may be detected by opposing positron emission detectors and define an LOR. LORs of the positron emission data may be classified by a processor to one or more calculated locations or location ranges of the calibration source and the patient (508). As discussed in more detail below, calculated positron emission locations may be classified by a processor using reference time offsets or a spatial filter (509). In some variations, the LORs are classified using positron emission data received within a coincidence time window of between about 6 nanoseconds and 10 nanoseconds.

Reference Time Offsets

The trajectory of a photon pair emitted by a positron annihilation event defines a LOR (e.g., a positron emission path). The origin of the annihilation event is at point located along the LOR and may be located using a difference in photon reception times (i.e., a time difference or time offset). In particular, a difference in reception times between the photons corresponds to a distance traveled by the photons along the LOR from the annihilation event. For example, if each photon of an annihilation event arrives at a respective detector at the same time, then the photons have traveled an equal distance such that the annihilation event originates at a midpoint of the LOR. Accordingly, in some variations, a positron emission (e.g., annihilation event) origin location corresponding to the calibration source and/or the patient may be calculated by a processor using TOF data (e.g., reception time difference of the pair of photons), LOR, and reference time offsets (510). For example, positron emission path data may be classified as originating from a calibration source (e.g., stationary radiation source) using a difference between a reception time of the pair of photons with a time threshold parameter range (e.g., time difference range) corresponding to the calibration source. Positron emission path data outside the time threshold parameter range may be classified as noise or as originating from the patient. In some variations, the positron emission detector may comprise a coincidence time resolution of at least about 300 picoseconds (ps) (FWHM) corresponding to a positional uncertainty of about 4.5 cm (FWHM) along the LOR.

In some of these variations, the calibration source may be distinguished from the positron emission data by comparing the difference in reception times (e.g., time difference or time offset) of a photon pair to a reference time offset corresponding to a location of the calibration source. For example, a look-up table (LUT) of reference time offsets (calculated using the equations discussed in detail below) may be stored in memory and compared to positron emission data. In some variations, a stationary calibration source may be located on a housing of a rotatable gantry relative to the PET detectors rotating about the patient scan or treatment region such that the time offset (e.g., time difference) is about 2.5 ns when PET detectors are located at specified gantry angles about the patient scan or treatment region. It should be understood that in other variations with different arrangements of PET detectors and/or emission properties calibration source(s), the time difference or time offset value corresponding to coincident photon originating from the calibration source may have different time difference values. In some variations, if the number of coincident photon events detected for time offsets other than 2.5 ns ("random" coincident photon events) is the same as, or greater than, the number of coincident photon events detected for a time offset of 2.5 ns ("true" coincident photon events), a fault signal may be generated. In some variations, the coincident photon events originating from the calibration source (e.g., the peaks centered around a time difference value of 2.5 ns in a histogram that plots the coincidence photon event count over a coincidence time window) may be distinguished from the coincident photon events originating from a PET-avid region in a patient using the spatial/sinogram filters described herein, optionally in combination with temporal filters that select for events with particular temporal characteristics (e.g., certain time difference values between the detection times of the two photons in a coincident event). In some variations, a passing criteria or threshold may be a ratio of the number of true coincident photon events to the number of random coincident photon events (true-to-random ratio value), where the value of the ratio is greater than or equal to one. It should be understood that while the examples described herein pertain to a system where the positron emission events detected by two rotatable PET detector arrays that originate from a single stationary calibration source have a time difference or offset value of about 2.5 ns, it should be understood that in other systems with different sizes and/or relative positions between the PET detector arrays and one or more calibration sources, the time difference or offset value may be any value (e.g., any value other than 2.5 ns). The width of the coincidence time window for detecting coincident photon events from either or both the calibration source(s) and/or PET-avid patient or phantom within the bore may be adjusted (e.g., expanded or narrowed relative to the examples described herein) as appropriate so that these coincident photon events may be extracted from the PET detector data. While the coincidence time window width may vary, the coincidence time window width may be centered around about 0 ns.

A. Stationary Calibration Source

In variations where a radiation treatment assembly comprises a rotatable gantry having mounted thereon positron emission detectors and a stationary housing coupled to a calibration source (e.g., FIGS. 2A-2B), a distance of the detector to the calibration source may vary as a function of gantry angle as the PET detectors rotate about a bore of the gantry. From a positron emission detector point-of-view (e.g., PET detector reference frame), the position of the PET detector is fixed as the calibration source rotates at a gantry angle theta ($\theta$) defined relative to a reference direction. With respect to the PET detector reference frame, the location of the detector may be defined by coordinates <x,y> where the X-axis corresponds to a horizontal axis plane (e.g., parallel to the ground and/or a patient support) and the Y-axis corresponds to a vertical plane perpendicular to the horizontal plane. The location of the calibration source may be defined as (r cos $\theta$, r sin $\theta$) where r represents a radius from a reference point (e.g., origin of the detector <x,y>) and $\theta$ is an angle from the reference direction. A location of a photon pair (e.g., first and second photons) detected by respective detectors may be defined as $<x_1,y_1>$ and $<x_2,y_2>$, respectively. A distance from the first and second photon detection location to the calibration source is given by:

$$d_1=\sqrt{(r\cos\theta-x_1)_2+(r\sin\theta\times y_1)^2}$$

$$d_2=\sqrt{(r\cos\theta-x_2)^2+(r\sin\theta-y_2)^2}$$

The first and second photons each travel at the speed of light (c) from the annihilation point to opposing positron emission detectors. A difference in reception time (i.e., a time difference or time offset) between the first and second photons is given by:

$$\Delta t=2*(d_1-d_2)/c$$

Accordingly, a table of reference time offsets $\Delta t$ may be calculated as a function of the gantry angle $\theta$ and photon pair distances $d_1$, $d_2$:

$$t(\theta,d_1,d_2)=\Delta t$$

A reference time offset may be compared to a corresponding detected photon pair time offset and a threshold parameter to generate a fault signal, as described in more detail below.

B. Annular Calibration Source

In other variations, an assembly may comprise a rotatable gantry having mounted thereon positron emission detectors and a stationary housing coupled to a calibration source such as the annular radiation source illustrated in FIG. 3. Each LOR of the stationary calibration source may originate from one of two locations (e.g., where the LOR intersects the annular radiation source). Therefore, the LUT includes two possible reference time offsets (e.g., locations) for each gantry angle $\theta$ and photon pair distances $d_1$, $d_2$ rather than a single reference time offset.

$$t(\theta,d_1,d_2)=\Delta t_1,\Delta t_2$$

For a stationary calibration source, a LUT stored in memory may comprise a pair of reference time offsets ($\Delta t_1$, $\Delta t_2$) for each set of gantry angle and photon pair distances. Due to the wide spatial and temporal separation between the two calibration source intersection points, a positron emission origin may be compared to the closest reference calibration source location with a small probability of error.

C. Rotating Calibration Source

In other variations, an assembly may comprise a rotatable gantry having mounted thereon both positron emission detectors and one or more calibration sources (e.g., radiation source, radiation source holder), such as illustrated in FIG. 4, where the calibration source is fixed relative to the positron emission detector. In this configuration, the distance of the calibration source to the detector does not vary (from a PET detector reference frame) and therefore does not require the LUT and calculations using the equations described above.

Patient Spatial Filter

In some variations, a positron emission origin location corresponding to the calibration source and/or the patient may be calculated using TOF data and one or more spatial filters. In other words, the calculated location of an annihilation event based on TOF data may be compared to reference locations or location ranges of the patient and calibration source and be used to classify the positron emissions and determine whether the coincident event originated from the patient or calibration source. In some variations, given the locations of a set of positron emissions, one or more spatial filters or classifiers may be applied to distinguish the positron emission data from the calibration source (e.g., radiation source and/or radiation source holder) and the patient (e.g., patient scan region). For example, a first spatial filter of the calibration source and a second spatial filter of the patient may be applied to distinguish the sources of the positron emission data. In some of these variations, positron emissions outside of the first and second spatial filters may be excluded as noise. The spatial filters may, for example, comprise a volume of the calibration source and/or patient and include a margin for error (predetermined or adjustable). In some variations, the margin may be from about 1 cm to about 10 cm. Alternatively or additionally, a spatial filter may designate a region within a bore of the system where the calibration source is expected to be located, and the processor may extract the LORs that intersect that region of the spatial filter but do not intersect the portion of the filter corresponding to the patient scan or treatment region, designating the extracted LORs as containing data pertaining the positron emission activity originating from the calibration source. In some variations, the processor may count the number of LORs that intersect that region of the spatial filter, and if that count does not meet or exceed a threshold of expected LORs (e.g., calculated based on the known radioactive and/or positron emission properties of the calibration source), a fault signal may be generated.

In some variations, the second spatial filter of the patient may comprise a geometry using a patient treatment plan including geometric and dosimetric parameters for radiation therapy treatment. For example, the patient treatment plan may comprise a set of target volumes (e.g., a patient region), including (in order of descending volume) an irradiated volume, treated volume, planning treatment volume (PTV), clinical target volume (CTV), and gross tumor volume (GTV). The PTV encompasses the GTV and adds a margin for error including patient alignment, machine calibration, and a motion envelope of the ROI. Positron emissions from the GTV may be used to direct radiation beamlets in EGRT while positron emissions outside of the GTV and otherwise within a volume of the PTV may be classified as noise. Position emissions located outside the PTV may be rejected altogether.

In some variations, the geometry of the spatial filter may be adjusted by a processor using the patient treatment plan (512). For example, the second spatial filter of the patient may automatically adjust the geometry of the second spatial filter to correspond to one of the GTV, CTV, and PTV, and may automatically adjust with modifications to the patient treatment plan. Additionally or alternatively, the spatial filter may be user adjustable such that a user such as an operator may input the volume of one or more of the first and second spatial filter.

In some variations, a processor may concurrently distinguish positron emission data from the calibration source and the patient using one or more spatial filters (514). For example, one or more of the first and second spatial filters may be applied to the positron emission data to classify the positron emission locations as corresponding to the calibration source and/or patient. Positron emission data located outside of a spatial filter (e.g., located outside a calibration region and/or patient region) may be excluded as noise. In some of these variations, a first spatial filter may be applied to the positron emission data and all other positron emissions (such as from the patient) may be excluded and disregarded.

Regardless of whether the positron emissions are classified using reference time offsets (510) or spatial filters (514), the positron emission data from the calibration source may be used by a processor to generate calibration data (e.g., a set of positron emission locations of the calibration source (516)). Optionally, the positron emission data from the patient may be used by a processor to generate patient data (e.g., a set of positron emission locations of the patient (518)). The patient data may be used to treat the patient (520) using, for example, a treatment radiation source under an EGRT procedure. It should be noted that steps (518, 520) are optional for PET detector calibration monitoring.

A calibrated positron emission detector should classify positron emissions from a calibration source at a location that matches the true location of the calibration source within a predetermined margin of error. A fault signal may be generated when a calculated location of the calibration source does not correspond to a reference location or location range of the calibration source. In particular, a fault signal may be generated (524) by a processor when the positron emission detector (e.g., calibration data) from the calibration source (e.g., radiation source, radiation source holder) exceeds a threshold parameter (522—Yes). In some variations, the threshold parameter may be a variability threshold parameter. For example, the variability threshold parameter may comprise a percentage of time that a calculated location of the calibration source is outside a reference location or location range (e.g., volume) of the calibration source (e.g., proportion of time when the calculated and reference locations or location ranges of the calibration source do not match). In some of these variations, a margin may be added to the reference location or location range. In some variations, a variability threshold may be about 0.1%, about 0.5%, about 1.0%, about 1.5%, about 2%, about 5%, and values in between. In some variations, calibration may be monitored continuously in time windows of about 1 seconds, about 10 seconds, about 10 seconds, and values in between. The variability threshold parameter may comprise one or more of a time threshold and/or location deviation threshold. Therefore, the fault signal may be generated when the positron emission data exceeds one or more of a time threshold and location deviation threshold. For example, a fault signal may be generated when a mean reception time offset ($\Delta t$) of positron emissions over a predetermined time window exceeds a time offset threshold parameter corresponding to a reference time offset value.

In some variations, calibration data (for a single stationary calibration source in a system with a rotatable gantry with two arrays of PET detectors, for example) may comprise the number of coincident photon events detected by one or more PET detectors over a specified time period and/or gantry rotation. The expected number of coincident photon events to be detected for each PET detector (e.g., each detector module or detector crystal) from the extracted LORs (i.e., LORs that intersect with the known location of the stationary calibration source) may be calculated based on the known properties of the calibration source as well as its location relative to the rotating PET detectors. The threshold parameter may be a tolerance or difference value between the detected number of LORs that intersect with the calibration source location and the expected number of coincident photons emitted from the calibration source. If the number of LORs detected by the PET detectors deviate from the expected number of expected emitted coincident photons by more than the specified tolerance or difference value, then a fault signal may be generated. For example, if the number of detected LORs per gantry angle position deviate from what is expected by more than the tolerance or difference threshold, and/or if the number of detected LORs over one or more gantry rotations deviate from what is expected by more than the tolerance or difference threshold, then a fault signal may be generated.

In some variations, alternatively or additionally, calibration data (for a single stationary calibration source in a system with a rotatable gantry with two arrays of PET detectors, for example) may comprise the number of coincident photons at particular energy levels (e.g., 511 keV) detected by one or more PET detectors over a specified time period and/or gantry rotation. The expected number of coincident photon events to be detected for each PET detector (e.g., each detector module or detector crystal) at various energy levels from the extracted LORs (i.e., LORs that intersect with the known location of the stationary calibration source) may be calculated based on the known properties of the calibration source as well as its location relative to the rotating PET detectors. The threshold parameter may be a tolerance or difference value between the detected number of coincident photons having an energy level of 511 keV and the expected number of coincident photons emitted from the calibration source having an energy level of 511 keV. If the number of coincident photons having an energy level of 511 keV detected by the PET detectors deviate from the expected number of expected emitted coincident photons having an energy of 511 keV by more than the specified tolerance or difference value, then a fault signal may be generated. For example, if the number of detected coincident photons having an energy level of 511 keV per gantry angle position deviate from what is expected by more than the tolerance or difference threshold, and/or if the number of detected coincident photons having an energy level of 511 keV over one or more gantry rotations deviate from what is expected by more than the tolerance or difference threshold, then a fault signal may be generated. For example, if no 511 keV coincident photons from LORs that intersect the location of the stationary calibration source are detected, a fault signal may be generated.

Figure 8A:
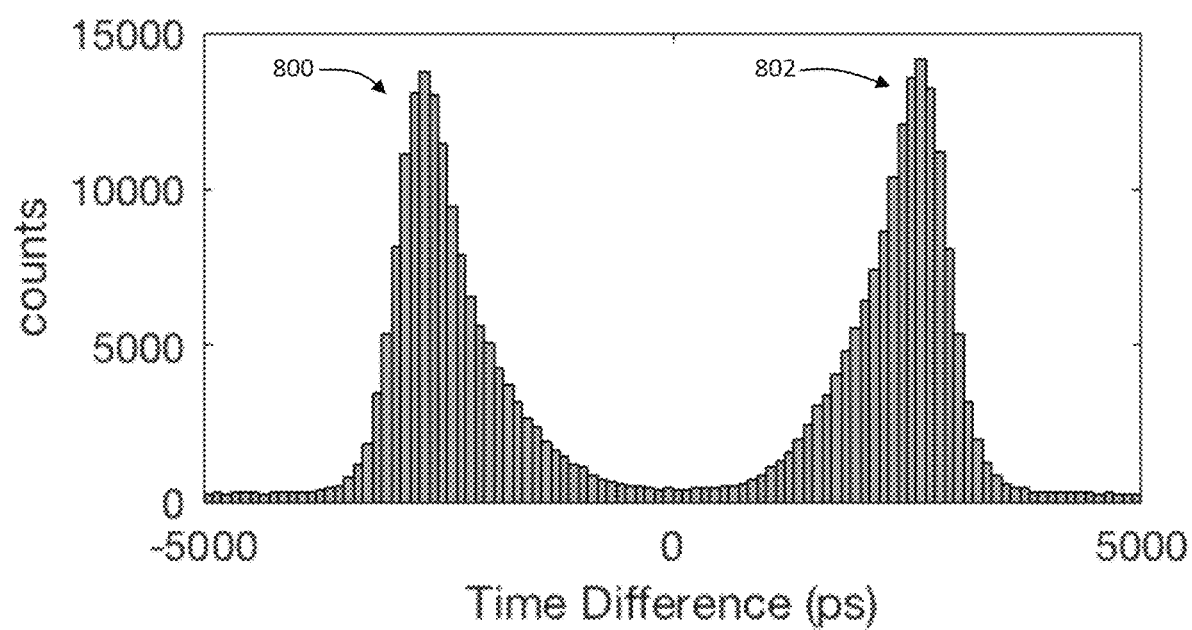
FIGS. 8A-8C are examples of histogram plots of coincident photon event counts over various coincidence time windows.

In some variations, alternatively or additionally, calibration data (for a single stationary calibration source in a system with a rotatable gantry with two arrays of PET detectors, for example) may comprise the number of coincident photon events detected that have specific time difference or offset values (i.e., the time difference between the detection of each of the photons in a coincident pair). The calibration data may include the number of coincident photon events detected over a range of time difference or offset values. This range of time difference or offset values may be referred to as a coincidence time window. In some variations, the number of coincident photon events may be measured over coincidence time windows having different ranges and/or centered over various time difference values, and/or over one or more gantry rotations. A histogram of coincident photon events measured in a coincidence time window may be generated by detecting coincident photon events using the PET detectors, comparing the detection time of each of the photons of a coincident pair to obtain a time difference value for each coincident photon event, and plotting (e.g., binning) the number of coincident photon events for each time difference value within the coincidence time window. Based on the known properties of the calibration source as well as its location relative to the rotating PET detectors, the number of coincident photon events having particular time difference values that correspond with the relative distances between the calibration source and each of the two arrays of PET detectors may be greater than the number of coincident photon events having other time difference values. For example, in a variation of a system where a stationary calibration source is located at the top or bottom of a bore (i.e., at a substantial distance away from the center of the bore and/or system isocenter) and the two PET detector arrays rotate and move relative to the stationary calibration source, the coincident photon events that originate from the calibration source may have a time difference value of, for example, 2.5 ns. In contrast, coincident photon events originating from a PET-avid region in a patient (i.e., close to the center of the bore and/or system isocenter) may have a time difference close to about 0 ns, since both annihilation photons will travel a similar distance before being detected by the first and second PET detector arrays. In some variations, the time difference of coincident photon events originating from a PET-avid region in a patient (or phantom) may be from about 0.1 ns to about 1.5 ns, e.g., about 0.25 ns, about 0.5 ns, about 0.75 ns, about 0.6 ns, about 1 ns, etc., depending on the geometry and location of the patient within the treatment and/or scanning region in the bore. FIG. 8A depicts one example of a system with a single calibration source at a bottom or top (i.e., edge region) of the bore, and two rotating PET detector arrays without a PET-avid region within the center of the bore, while FIG. 8B depicts an example of a system similar to that of FIG. 8A, but with a PET-avid region within the center of the bore (e.g., a PET-avid phantom or patient), resulting in a peak centered around the time difference value 0 ns.

In some variations, the coincident photon events detected over a range of time differences centered around the time difference value of 0 ns may be classified as "true" coincident photon events, while the coincident photon events detected over a range of time differences centered around a non-zero time difference value may be classified as "random" coincident photon events. For example, if the relative positions of the PET detector arrays and the stationary calibration source give rise to coincident photon events with a time difference of 2.5 ns, then "true" coincident photon events may be events detected within a coincidence time window that includes time difference values between −2.5 ns and +2.5 ns (centered around a time difference value of 0 ns). Alternatively or additionally, a coincidence time window comprising "true" coincident photon events may have a range of time difference values from −5 ns to +5 ns. Random coincident photon events may be events detected within a coincidence time window between 15 ns and 25 ns (centered around a time difference value of 20 ns), or any time window that is centered around a non-zero time difference value and does not overlap with the "true" coincidence time window. If the number of coincident photon events in the "random" coincidence time window is the same as, or greater than, the number of coincident photon events in the "true" coincidence time window, a fault signal may be generated. In some variations, a threshold criterion may be a ratio of the number of coincident photon events in the "true" coincidence time window (e.g., a first coincidence time window centered around a 0 ns time difference or offset) to the number of coincident photon events in the "random" coincidence time window (e.g., a second coincidence time window centered around a non-zero photon reception time difference or offset with a range that does not overlap with the first coincidence time window). This ratio may be referred to as a true-to-random ratio value, where a passing threshold criterion may be a ratio value that is greater than or equal to one. If the true-to-random ratio value does not meet or exceed one, then a fault signal may be generated. The true-to-random ratio value may be calculated by counting the number of coincident photon events within the first coincidence time window (e.g., number of true events), counting the number of coincident photon events within the second coincidence time window (e.g., number of random events), and dividing the number of true events by the number of random events. FIGS. 8A-8C depict plots (e.g., histograms) that represent the number (counts) of coincident photon events detected for various coincidence time window widths. FIG. 8A depicts one example of a histogram or plot of the number of true coincident photon events detected within a first (true) coincidence time window have a range between −5 ns and 5 ns for a stationary calibration source (no PET-avid patient) over one or more gantry rotations. As may be seen there, there are two peaks within the coincidence time window, each of the peaks centering around +/−2.5 ns, respectively. The first peak (800) centered around −2.5 ns represents the number of coincident photon events detected at a first gantry location of the first array of PET detectors where the first array of PET detectors is located at its closest distance to the calibration source (i.e., while the second array of PET detectors is located at a significantly greater distance away from the calibration source). The second peak (802) centered around +2.5 ns represents the number of coincident photon events detected at a second gantry location of the second array of PET detectors where the second array of PET detectors is located at its closest distance to the calibration source (i.e., while the first array of PET detectors is located at a significantly greater distance away from the calibration source).

Figure 8B:
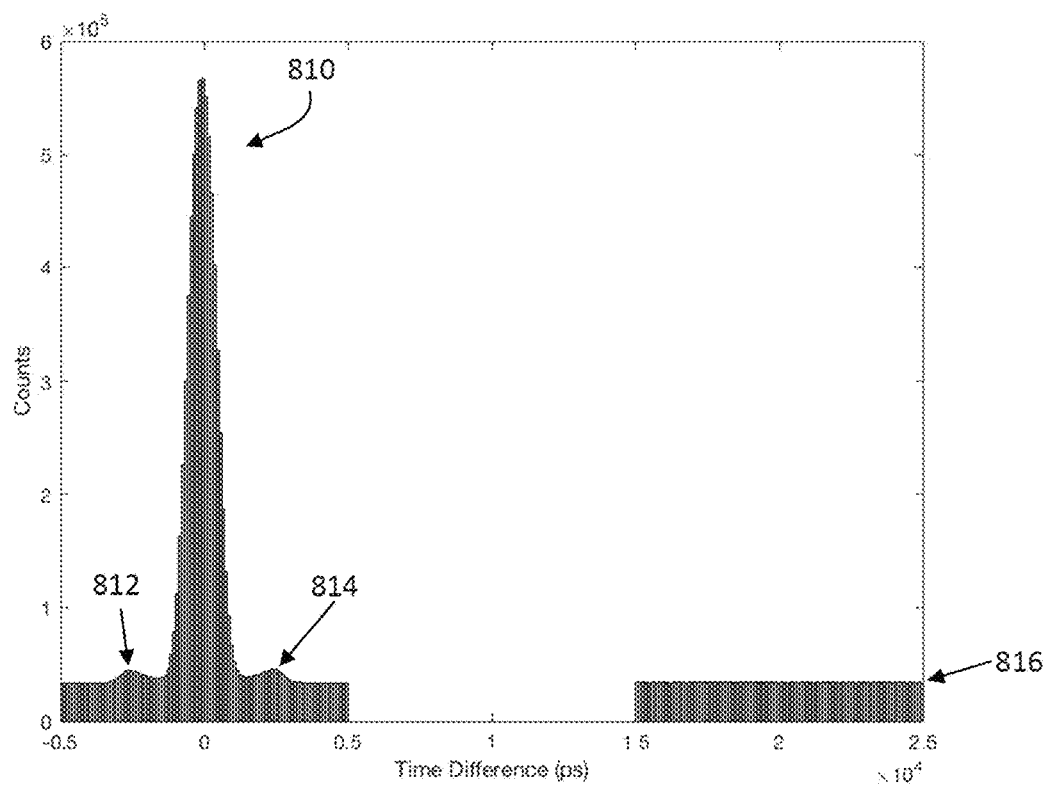
Figure 8C:
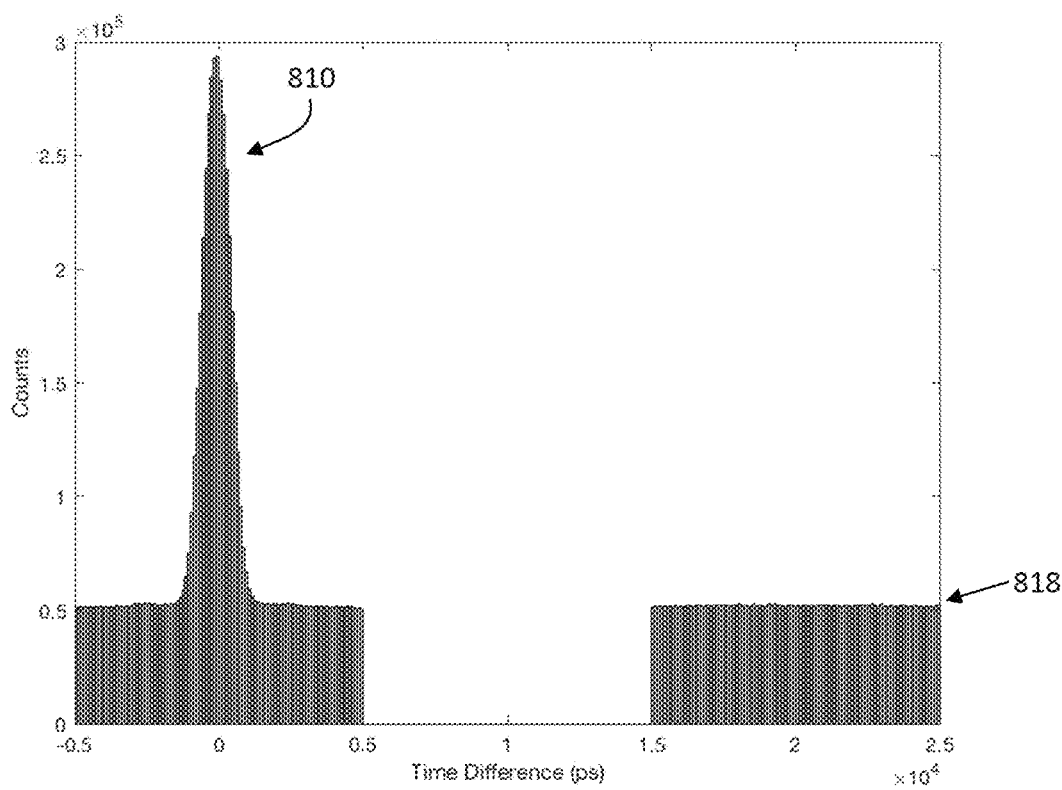

FIGS. 8B and 8C depict similar plots, but in addition to the calibration source, also include a patient with a PET-avid region (e.g., a tumor region that has elevated levels of PET activity due to preferential uptake of a PET tracer). The peak (810) centered around the time difference value of about 0 ns represents the coincident photon events detected that originate from the patient. In these examples, the first (true) coincidence time window may be between −5 ns and 5 ns, centered around 0 ns. The second (random) coincidence time window may be between 15 ns and 25 ns, centered around 20 ns. FIG. 8B depicts one variation of a system where the PET detectors are functioning properly and/or calibrated as desired. As may be seen there, within this first coincidence time window, the two peaks (812, 814) centered around −/+2.5 ns represent the coincident photon events originating from the calibration source and detected by the PET detectors. The number of "random" coincident photon events (816) in the second coincidence time window (e.g., between 15 ns and 25 ns, centered around 20 ns) is less than the number of coincident photon events in the first coincidence time window; that is, the true-to-random ratio is about one or more. FIG. 8C depicts one variation of a system where the PET detectors are not functioning properly and/or are no longer calibrated as desired. As may be seen there, there are no peaks centered around −/+2.5 ns in the first (true) coincidence time window (between −5 ns to 5 ns), and the number of "random" coincident photon events (818) in the second (random) coincidence time window (between 15 ns and 25 ns, centered around 20 ns) is greater than or equal to the number of coincident photon events having a time difference of about 2.5 ns; that is, the true-to-random ratio is less than or equal to one. Since the peaks are not identifiable, and/or are below a threshold value (i.e., less than the number of random coincident photon events), a fault signal may be generated. In some variations, a threshold criterion for a passing true-to-random ratio may be a ratio value that is greater than one (e.g., about 1.1 or more, about 1.2 or more, about 1.3 or more, about 1.5 or more, etc.) and a fault signal may be generated if the actual/calculated true-to-random ratio is less than that ratio value (e.g., less than about 1.1, less than about 1.2, less than about 1.3, less than about 1.5, etc., respectively). For example, if the threshold ratio value is 1.2, a fault signal may be generated if the actual true-to-random ratio is calculated to be 1.1 or 1. The generation of a fault signal may include generating a notification to the user to check the calibration and/or proper functioning of the PET detectors, and/or gantry motion sensors, and/or to check or further characterize the PET tracer uptake by the patient.

The calibration monitoring of the PET detectors disclosed herein is based on a direct measurement of the detectors and may optionally be used to corroborate and/or verify other sensors in the radiation therapy assembly. For example, the radiation therapy assembly may comprise one or more temperature sensors that monitor the temperature of the PET detectors. In systems without a positron-emitting calibration source, these temperature readings may be used as an indicator of PET detector function. For example, the temperature of the positron emission detectors may be measured using one or more temperature sensors, and if the temperature exceeds a threshold value (e.g., an increase of 2 degrees during a procedure), a fault signal may be generated. However, monitoring PET detector function by measuring only secondary factors (such as temperature) may result in an inaccurate assessment if any of the sensors fail (especially due to the high-radiation environment in the vicinity of a radiation therapy assembly). That is, a fault signal based on temperature measurements may be the result of a fault in one or more positron emission detectors and/or a fault in a temperature sensor. Calibration monitoring of the PET detectors using a positron-emitting calibration source as described herein allows for a separate verification of a fault signal generated by the temperature sensor(s). This may provide two independent checks on positron emission detector calibration and increase confidence in calibration monitoring. Alternatively or additionally, a radiation therapy assembly may comprise one or more sensors that monitor parameters and various subsystem of the therapy assembly. Some radiation therapy assemblies may monitor the temperature of other portions of the radiation therapy assembly (e.g., gantry, imaging source and detector, multi-leaf collimator, bore volume, regions in the vicinity of the PET detectors, etc.), the flowrate of a cooling fluid (using one or more flow meters), and/or ambient and/or scattered radiation levels (using one or more radiation detectors such as scintillation counters, Gieger counters, gaseous ionization detectors, ionization chambers, and the like). Data readings from one or more of the sensors may be used in conjunction with calibration source emission data to assess and/or adjust one or more of the PET detectors. A fault signal generated based on signals detected by the PET detectors may also trigger a user to check the calibration of the motion and/or position sensors and/or position encoders of a rotatable gantry.

A radiation treatment assembly may respond in one or more ways in response to the generation of a fault signal (524). For example, the radiation treatment assembly may deactivate one or more positron emission detectors, output the detector status to an operator, stop an imaging and/or radiation therapy treatment procedure, and calibrate the detector using the calibration data. In some variations, an interlock may be generated and visually represented on a display to the user. For example, a visual or graphical user interface depicted on a display or monitor may comprise a status bar or icon of each subsystem of the radiation treatment assembly. The appearance of the status bar or icon may be updated at regular time intervals and/or as desired by the user. When a fault signal is generated and an interlock is triggered, the status bar or icon for that subsystem may change color (e.g., turn red). The user may then click on the status bar or icon to obtain a description of the error and/or to commence further testing and/or calibration of that subcomponent. When a fault is detected using one or more of the methods described herein, the icon for the PET detectors (e.g., one icon per PET detector array), and/or the icon for the gantry motion/position encoders, and/or the icon for the calibration source, and any other subsystem may change color or form. The user may click on any one of the icons to troubleshoot or obtain further details about the status of that subsystem. Alternatively or additionally, a fault signal may also prompt the user to confirm that the PET tracer was properly introduced to the patient.

In some variations, the fault signal may comprise one or more positron emission detectors at fault. The number of faulty detectors may be compared to a predetermined threshold (526) to determine which faulty detectors to deactivate. In some of these variations, at least one of the positron emission detectors of a first and second array of the detectors may be deactivated based on the fault signal (528, 530). In one example, up to three positron emission detectors may be deactivated based on the fault signal indicating fault in up to three of the positron emission detectors (528). Conversely, each of the first array and second array of detectors may be deactivated based on the fault signal indicating fault in four or more of the detectors (530). Deactivating a subset of the positron emission detectors allows patient imaging and/or radiation therapy treatment to continue when some of the positron emission detectors are uncalibrated. It should be appreciated that the threshold number of faulty detectors may be any number of detectors. For example, if even a single PET detector is faulty or uncalibrated, the delivery of treatment radiation may be paused and/or the treatment session may be stopped.

In some variations, radiation therapy treatment of the patient using the treatment radiation source may be stopped (532) in response to the fault signal. For example, radiation therapy treatment may be stopped within about 0.01 seconds after the fault signal is generated, thereby significantly reducing potential harm to the patient due to loss of calibration of one or more positron emission detectors. Conventional quality assurance (QA) procedures that verify calibration once a day are unable to monitor PET detector calibration in real-time.

In some variations, the radiation treatment assembly may undergo a QA procedure to verify the fault signal and then recalibrate the faulty detectors if necessary. One or more positron emission detectors may be calibrated by a processor using the calibration data (534). For example, a processor may recalibrate one or more of the positron emission detectors (e.g., dynamic range of light detectors) by compensating for a consistent time offset error in the calibration data. Other aspects of the one or more positron emission detectors that may be adjusted or corrected may include energy calibration, energy resolution, detector count-rate uniformity, and/or dead-time corrections.

In some variations, a detector status may be output (536) based on one or more of the fault signal, positron emission detector deactivation, radiation therapy treatment status, and positron emission detector calibration. One or more visual, audio, and tactile sensory output systems coupled to the radiation treatment assembly may be used to output the detector status to a user such as an operator. For example, a display coupled to the radiation treatment assembly may display the detector status to an operator. A detector status may be output continuously, at predetermined intervals, upon a change in status, and upon generating a fault signal. Additionally or alternatively, the detector status may be stored in memory and/or transmitted over a network to be output and/or displayed to one or more of a remote operator, system vendor, regulatory agency, and/or stored in a database.

Some variations described herein relate to a computer storage product with a non-transitory computer-readable medium (also may be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also may be referred to as code or algorithm) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical discs; solid state storage devices such as a solid state drive (SSD) and a solid state hybrid drive (SSHD); carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other variations described herein relate to a computer program product, which may include, for example, the instructions and/or computer code disclosed herein.

The systems, devices, and/or methods described herein may be performed by software (executed on hardware), hardware, or a combination thereof. Hardware modules may include, for example, a general-purpose processor (or microprocessor or microcontroller or multi-core processor), a field programmable gate array (FPGA), and/or an application specific integrated circuit (ASIC). Software modules (executed on hardware) may be expressed in a variety of software languages (e.g., computer code), including C, C++, Java®, Ruby, Visual Basic®, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code.

Although the foregoing variations have, for the purposes of clarity and understanding, been described in some detail by of illustration and example, it will be apparent that certain changes and modifications may be practiced, and are intended to fall within the scope of the appended claims. Additionally, it should be understood that the components and characteristics of the systems and devices described herein may be used in any combination. The description of certain elements or characteristics with respect to a specific figure are not intended to be limiting or nor should they be interpreted to suggest that the element cannot be used in combination with any of the other described elements. For all of the variations described above, the steps of the methods may not be performed sequentially. Some steps are optional such that every step of the methods may not be performed.

The invention claimed is:

1. A method for monitoring PET detector function during a radiotherapy session, the method comprising:
    acquiring positron emission data using one or more PET detectors during delivery of radiation therapy;
    extracting positron emission data representing positron emission activity from a calibration source;
    determining whether one or more PET detectors are faulty based on the extracted positron emission data; and
    generating a fault signal if one or more PET detectors are faulty.

2. The method of claim 1, wherein determining whether the one or more PET detectors are faulty comprises determining whether the extracted positron emission data meets a pre-determined criterion.

3. The method of claim 2, wherein the pre-determined criterion comprises a spatial filter that selects for positron emission data originating from a location of the calibration source, and wherein determining whether one or more PET detectors is faulty comprises applying the spatial filter to the extracted positron emission data and determining whether the filtered positron emission data co-localizes with the location of the calibration source.

4. The method of claim 3, wherein the spatial filter is adjustable.

5. The method of claim 2, wherein the pre-determined criterion comprises a threshold number of coincident photon events detected with a first time difference, and wherein determining whether one or more PET detectors are faulty comprises generating a plot of an actual number of coincident photon events detected with the time difference, and wherein a fault signal is generated when the actual number of coincident photon events occurring with the time difference does not exceed the threshold number.

6. The method of claim 1, wherein extracting positron emission data comprises calculating a location of the calibration source using the acquired positron emission data and wherein determining whether one or more PET detectors are faulty comprises determining whether the calculated location of the calibration source sufficiently corresponds to a location of the calibration source.

7. The method of claim 6, wherein calculating the location of the calibration source uses a spatial filter.

8. The method of claim 1, wherein the extracted positron emission data comprises PET detector calibration data.

9. The method of claim 8, wherein the PET detector calibration data comprises one or more of spatial resolution data, temporal resolution data, energy sensitivity data, energy precision data, a number of detected lines-of-response (LORs) that intersect with a location of the calibration source, and/or energy levels of the detected LORs.

10. The method of claim 8, wherein determining whether one or more PET detectors are faulty comprises determining whether the PET detector calibration data exceeds a threshold parameter.

11. The method of claim 1, further comprising one or more of pausing the delivery of radiation therapy, performing diagnostics on the one or more PET detectors, de-activating the one or more PET detectors, and/or recalibrating the one or more PET detectors if one or more of the PET detectors are faulty.

12. The method of claim 11, wherein recalibrating the one or more PET detectors occurs after pausing the delivery of radiation therapy.

13. The method of claim 1, wherein extracting positron emission data comprises classifying positron emission data as originating from the calibration source or not originating from the calibration source.

14. The method of claim 13, wherein classifying positron emission data uses reference time offsets and/or a spatial filter.

15. The method of claim 1, further comprising measuring a temperature of the one or more PET detectors, and wherein determining whether a sensor is faulty further comprises determining whether the measured temperature exceeds a threshold value.

16. The method of claim 1, further comprising identifying which of the one or more PET detectors is faulty and de-activating the faulty PET detector(s).

17. The method of claim 1, wherein the fault signal comprises an interlock having a graphical user interface.

18. The method of claim 1, further comprising de-activating up to three faulty PET detectors.

19. The method of claim 1, further comprising de-activating all of the PET detectors if one or more PET detectors are determined to be faulty.

\* \* \* \* \*